United States Patent [19]

Morris

[11] Patent Number: 5,252,735
[45] Date of Patent: Oct. 12, 1993

[54] ANTIATHEROSCLEROTIC AND ANTITHROMBOTIC 2-AMINO-6-PHENYL-4H-PYRAN-4-ONES

[75] Inventor: Joel Morris, Kalamazoo, Mich.

[73] Assignee: The Upjohn Company, Kalamazoo, Mich.

[21] Appl. No.: 842,020

[22] Filed: Feb. 25, 1992

Related U.S. Application Data

[63] Continuation-in-part of Ser. No. 545,935, Jun. 29, 1990, abandoned.

[51] Int. Cl.$^5$ .................. C07D 309/38; C07D 405/04
[52] U.S. Cl. ..................... 544/121; 544/124; 544/128; 544/130; 544/141; 544/149; 544/353; 546/207; 546/174; 548/201; 549/419
[58] Field of Search ............... 544/121, 124, 128, 130, 544/141, 149, 353; 514/231.5, 235.2, 235.5, 326; 546/207, 174; 549/419; 548/201

[56] References Cited

U.S. PATENT DOCUMENTS

| | | | |
|---|---|---|---|
| 3,029,256 | 4/1962 | Cook | 544/149 |
| 3,419,555 | 12/1968 | Jenkins | 544/149 X |
| 3,468,915 | 9/1969 | Tate | 544/149 X |

FOREIGN PATENT DOCUMENTS 3528601 2/1987 Fed. Rep. of Germany .

WO90/06921 6/1990 World Int. Prop. O. .

OTHER PUBLICATIONS

Capuano, L. et al., "Reactions of 2-Diazo-1,3-diketones with Enamines and Ketene-N,O-Acetals, II," Chem. Ber. 109:3497-3504 (1976).

*Primary Examiner*—Joseph Paul Brust
*Assistant Examiner*—Jacqueline Haley
*Attorney, Agent, or Firm*—Donald Corneglio

[57] ABSTRACT

This invention relates to compounds of Formula I

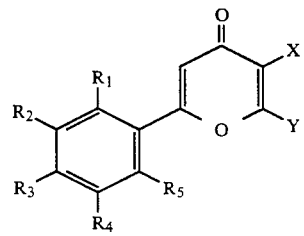

which are useful as antiatherosclerotic agents and inhibitors of cell proliferation for the treatment of proliferative diseases. In addition, various compounds of Formula I are useful inhibitors of platelet aggregation.

7 Claims, No Drawings

ANTIATHEROSCLEROTIC AND ANTITHROMBOTIC 2-AMINO-6-PHENYL-4H-PYRAN-4-ONES

CROSS-REFERENCE TO RELATED APPLICATIONS

This application is the continuation of PCT/US91/03659 abandoned which was a continuation-in-part of U.S. Ser. No. 07/545,935 filed Jun. 29, 1990, abandoned.

BACKGROUND OF THE INVENTION

The present invention is directed toward 2-amino-6-phenyl-4H-pyrano-4-ones which are pharmacologically active compounds. They have been shown to be inhibitors of cell proliferation in fibroblasts and therefore may be useful for the treatment or prevention of atherosclerosis as well as proliferative diseases. The compounds of the subject invention are further useful in the prevention or treatment of thrombotic diseases as they have been shown to inhibit ADP-induced platelet aggregation.

Atherosclerosis in mammals is a disease characterized by the deposition of atherosclerotic plaque on arterial walls. While atherosclerosis exhibits many varied forms and consequences, typical consequences of atherosclerotic diseases include angina pectoris, myocardial infarction, stroke and transient cerebral ischemic attacks. Other forms of atherosclerotic diseases include certain peripheral vascular diseases and other ischemias (e.g., bowel and renal).

Medical science now recognizes that certain forms of atherosclerosis may be preventable or reversible. Agents capable of preventing or reversing atherosclerosis are characterized as exhibiting antiatherosclerotic activity. Since serum lipids have a recognized association with atherogenesis, an important class of antiatherosclerotic agents are those with serum lipid-modifying effects. Serum lipids implicated in atherogenesis include serum cholesterol, serum triglycerides, and serum lipoproteins.

With respect to serum lipoproteins, at least three different classes of these substances have been characterized: high density lipoproteins (HDL's), low density lipoproteins (LDL's), and very low density lipoproteins (VLDL's). HDL's are often referred to as alphalipoproteins, while LDL's and VLDL's are referred to as betalipoproteins. The enhancement of HDL levels (hyperalphalipoproteinemic activity) is postulated to have direct antiatherosclerotic effects. See Eaton, R. P., J. Chron. Dis 31:131-135 (1978). In contrast, agents which reduce serum LDL's and serum VLDL's (hypobetalipoproteinemic agents) are also associated with antiatherogenic effects. See Haust, M. D., "Reaction Patterns of Intimal Mesenchyme to Injury and Repair in Atherosclerosis", Adv. Exp. Med. Biol. 43:35-57 (1974), which postulates that serum LDL is a factor in atherosclerotic lesion formation.

Numerous animals models have been developed for assessing antiatherosclerotic activity. Principal among these are models for assessing hypolipoproteinemic activity in the rat and antiatherosclerotic activity in the Japanese quail. For a description of the operation of the hypobetalipoproteinemic rat model, refer to the known methods of Schurr, P. E., et al., "High Volume Screening Procedure for Lypobetalipoproteinemia Activity in Rats", Adv. Exp. Med. Biol. 67: Atherosclerotic Drug Discovery, pp. 215-229, Plenum Press (1975). For a description of the Japanese quail model, see Day, C. E. et al., "Utility of a Selected Line (SEA) of the Japanese Quail (Corturnic Corturnix japonica) for the Discovery of New Anti-Atherosclerosis Drugs", Laboratory Animal Science 27:817-821 (1977).

While various compounds are known to have antiproliferative and antiplatelet activity the subject compounds are structurally unique. Chem. Ber., 109(11), 3497-3504 (1976) reports a 6-(dimethylamino)-2,3-diphenyl-4H-pyran-4-one which has a diphenyl substituted pyrone ring.

SUMMARY OF THE INVENTION

The present invention is directed toward compounds of Formula I which are useful in association with a pharmaceutical carrier as a medicament in the prevention or treatment of atherosclerosis or thrombotic diseases. In addition, various compounds of the Formula I are useful inhibitors of cell proliferation and/or platelet aggregation.

In one aspect, this invention is represented by compounds of Formula I

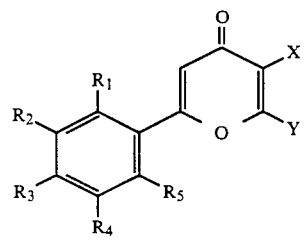

or pharmaceutically acceptable salts thereof wherein
X is hydrogen, $C_1$-$C_5$ alkyl, or a halogen atom; Y is selected from the group consisting of —$(CH_2)_n NR_9 R_{10}$ wherein $R_9$ and $R_{10}$, being the same or different, are selected from the group consisting of (a) hydrogen, preferably $R_9$ and $R_{10}$ are not both hydrogen; (b) $C_1$-$C_{12}$ alkyl; (c) phenyl optionally substituted with one, 2 or 3 $C_1$-$C_4$ alkyl, $C_1$-$C_4$ alkoxy, halo, OH, trifluoromethyl or —$CO_2(C_1$-$C_4$ alkyl); (d) —$(CH_2)_q$phenyl wherein phenyl is optionally substituted with one, 2 or 3 $C_1$-$C_4$ alkyl, $C_1$-$C_4$ alkoxy, halo, OH, trifluoromethyl or —$CO_2(C_1$-$C_4$alkyl), (e) —$(CH_2)_n$pyridinyl or (f) wherein $R_9$ and $R_{10}$, taken together with N, form a saturated or unsaturated heterocyclic amine ring selected from the group consisting of:
(aa) 4-morpholine optionally substituted with one or two members selected from the group consisting of $C_1$-$C_4$ alkyl, $C_1$-$C_4$ alkoxy, halo or trifluoromethyl,
(bb) 4-thiomorpholine optionally substituted with one or two members selected from the group consisting of $C_1$-$C_4$ alkyl, $C_1$-$C_4$ alkoxy, halo or trifluoromethyl,
(cc) 3-amino-1-pyrrolidine,
(dd) 1-pyrrolidine optionally substituted with one or two members selected from the group consisting of $C_1$-$C_4$ alkyl, $C_1$-$C_4$ alkoxy, halo, OH, —$CH_2OH$, or trifluoromethyl,
(ee) 1-piperidine optionally substituted with one or two members selected from the group consisting of $C_1$-$C_4$ alkyl, $C_1$-$C_4$ alkoxy, halo, trifluoromethyl, —$(CH_2)_q OH$, —$CO_2H$, —$CO_2CH_3$, —CO₂CH₂CH₃ or phenyl (wherein phenyl is optionally substituted with one, 2 or 3 $C_1$-$C_4$ alkyl, $C_1$-$C_4$ alkoxy, halo or trifluoromethyl), (ff) 1-piperazine, 4-methyl-1-piperazine 4-(cycloC₃-C₆alkyl)-1-piperazine, 4-phenyl-1-piperazine (wherein phenyl is optionally substituted with one, 2 or 3 $C_1$-$C_4$ alkyl, $C_1$-$C_4$ alkoxy, halo or trifluoromethyl) or 4-pyridinyl-1-piperazine optionally substituted with one or two members selected from the group consisting of $C_1$-$C_4$ alkyl, $C_1$-$C_4$ alkoxy, halo, OH, trifluoromethyl, —CH₂OH, —CO₂CH, —CO₂CH₃ or —CO₂CH₂CH₃, and (gg) thiazolidine, thiazolidine-4-carboxylic acid, pipecolinic acid, p-piperazinacetophenone, 1-piperazine, 1-methylpiperazine, 4-phenyl-1,2-3,6-tetrahydropyridine, proline, tetrahydrofurylamine, 1-(3-hydroxy)pyrrolidine, nipecotamide, 1,2,3,4-tetrahydroisoquinoline or imidazole;

$R_1$, $R_2$, $R_3$, $R_4$ and $R_5$ are independently selected from the group consisting of: hydrogen, $C_1$-$C_8$ alkyl, —(CH₂)ₙphenyl (wherein phenyl is optionally substituted with one, 2 or 3 $C_1$-$C_4$ alkyl, $C_1$-$C_4$ alkoxy, halo, OH, trifluoromethyl or —CO₂($C_1$-$C_4$alkyl)), —(CH₂)ₙnaphthyl, —(CH₂)ₙpyridinyl, —(CH₂)qNR₉R₁₀, —CH=CH-phenyl (wherein phenyl is optionally substituted with one, 2 or 3 $C_1$-$C_4$ alkyl, $C_1$-$C_4$ alkoxy, halo, OH, trifluoromethyl or —CO₂($C_1$-$C_4$alkyl)),

—CH₂—CH=CH₂,

—CH=CH—CH₃,

—O—CH₂—CH=CH₂,

—C≡C-phenyl (wherein phenyl is optionally substituted with one, 2 or 3 $C_1$-$C_4$ alkyl, $C_1$-$C_4$ alkoxy, halo, OH, trifluoromethyl or —CO₂($C_1$-$C_4$alkyl)), —O(CH₂)p(N-methylpiperdin-3-yl), —O—(CH₂)pNR₉R₁₀,

—O—CH₂CH(OCH₃)₂,

—O—(CH₂)pOR₁₅ (wherein R₁₅ is selected from $C_1$-$C_5$ alkyl, —(CH₂)ₙphenyl (phenyl optionally substituted with one, 2 or 3 $C_1$-$C_4$ alkyl, $C_1$-$C_4$ alkoxy, halo, OH, trifluoromethyl or —CO₂($C_1$-$C_4$alkyl)), —(CH₂)ₙpyridin-yl or —(CH₂)ppiperidin-1-yl),

—(CH₂)ₙC(O)—(CH₂)ₙR₉,

—(CH₂)ₙC(O)O—(CH₂)ₙR₉,

—(CH)ₙC(O)O—(CH₂)pNR₉R₁₀,

—(CH₂)ₙC(O)(CH₂)ₙNR₉R₁₀,

NO₂,

—O—(CH₂)ₙC(O)—(CH₂)ₙR₉,

—O—(CH₂)ₙC(O)O—(CH₂)ₙR₉,

—O—(CH₂)ₙC(O)—(CH₂)ₙNR₉R₁₀,

—NR₉R₁₀,

—N(R₉)(CH₂)ₙC(O)—(CH₂)ₙR₁₀,

—N(R₉)—(CH₂)ₙC(O)O—(CH₂)ₙR₁₀,

N(R₉)(CH₂)ₙC(O)—(CH₂)ₙNR₉R₁₀,

—OCH(nBu)phenyl,

—O—(CH₂)ₙphenyl (wherein phenyl is optionally substituted with one, 2 or 3 $C_1$-$C_4$ alkyl, $C_1$-$C_4$ alkoxy, halo, OH, trifluoromethyl or —CO₂($C_1$-$C_4$alkyl)), —O—(CH₂)ₙpyridine, —O(CH₂)ₙC(O)—(CH₂)ₙpyridine, —O—(CH₂)ₙC(O)O—(CH₂)ₙpyridine, —O(CH₂)ₙC(O)—N(R₉)(CH₂)ₙpyridine, —O—(CH₂)ₙquinoxalinyl, —O—(CH₂)ₙquinolinyl, —O—(CH₂)ₙpyrazinyl, —O—(CH₂)ₙnaphthyl, —O—(CH₂)ₙC(O)—(CH₂)ₙnaphthyl, —O—(CH₂)ₙC(O)O—(CH₂)ₙnaphthyl, —O—(CH₂)ₙC(O)NR₉—(CH₂)ₙnaphthyl, halo (fluoro, chloro, bromo, iodo),

OH,

—(CH₂)q—OH, (CH₂)qOC(O)R₉,

—(CH₂)qOC(O)—NR₉R₁₀,

-(1-cyclohexyl-1H-tetrazol-5-yl)$C_1$-$C_4$ alkoxy,

-(1-($C_1$-$C_5$alkyl)-1H-tetrazol-5-yl)$C_1$-$C_4$ alkoxy,

-(1-(phenyl)-1H-tetrazol-5-yl) $C_1$-$C_4$ alkoxy (wherein phenyl is optionally substituted with one, 2 or 3 $C_1$-$C_4$ alkyl, $C_1$-$C_4$ alkoxy, halo, OH, trifluoromethyl or —CO₂($C_1$-$C_4$alkyl)), -(1-(pyridinyl)-1H-tetrazol-5-yl)$C_1$-$C_4$ alkoxy, -(1-(1-phenylethyl)-1H-tetrazol-5-yl)$C_1$-$C_4$ alkoxy, -$C_1$-$C_4$ alkoxyl;

n is 0-5 (preferably 0 or one);

p is 2-5 (preferably 2 or 3); and q is 1-5 (preferably 1 or 2).

In another aspect, this invention is represented by compounds of Formula II

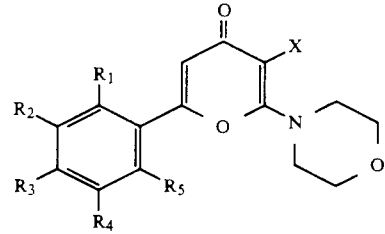

as defined above or pharmaceutically acceptable salts thereof. The compounds of Formula I and II are useful in the inhibition of cell proliferation and therefore are useful in the treatment of diseases whose mechanism of action is the proliferation of cells.

DETAILED DESCRIPTION OF THE INVENTION

The present invention is directed toward compounds of Formulas I and II as defined above and which are pharmaceutically useful for treating atherosclerosis, and thrombotic proliferative diseases.

The carbon content of various hydrocarbon containing moieties is indicated by a prefix designating the minimum and maximum number of carbon atoms in the moiety, i.e., the prefix $C_i$-$C_j$ indicates a carbon atoms content of the integer "i" to the integer "j" carbon atoms, inclusive. Thus, $C_1$-$C_3$ alkyl refers to alkyl of 1-3 carbon atoms, inclucive, or methyl, ethyl, propyl, and isopropyl.

With respect to the above, $C_1$-$C_4$alkyl is methyl, ethyl, propyl, or butyl, including isomeric forms thereof. Similarly, $C_1$-$C_6$ alkyl is methyl, ethyl, propyl, butyl, pentyl, hexyl, and isomeric forms thereof.

The term "halo" includes fluoro, chloro, bromo and iodo.

Examples of $C_1$-$C_8$ alkylthiomethyl are methylthiomethyl, ethylthiomethyl, propylthiomethyl, butylthiomethyl, pentylthiomethyl, hexylthiomethyl, and heptylthiomethyl, and isomeric forms thereof.

Examples of $C_1$-$C_8$ alkoxymethyl are methoxymethyl, ethoxymethyl, propoxymethyl, butoxymethyl, pentoxymethyl, butoxymethyl, pentoxymethyl, hexoxymethyl, and heptoxymethyl, and isomeric forms thereof.

Examples of heterocylic amines corresponding to heterocyclic amine rings according to —$NR_9R_{10}$ are:
4-morpholine,
4-phenyl-1-piperazine,
4-(2-pyridinyl)-1-piperazine,
2,6-dimethyl-4-morpholine,
1-pyrrolidine,
4-methyl-1-piperazine,
1-piperidine,
4-phenyl-1-piperidine
thiazoline,
3-piperidine methanol,
2-piperidine methanol,
pipecolic acid,
3-piperidine ethanol,
2-piperidine ethanol,
1-piperazine propanol,
p-piperazinoacetophenone,
4-phenyl-1,2,3,6-tetrahydropyridine,
4-phenylpiperidine,
proline,
1-(3-hydroxy)pyrrolidine,
tetrahydrofurylamine,
pyrrolidimethanol,
3-pyrroline,
thiazolidine-4-carboxylic acid,
thiomorpholine,
nipecotamide,
2-methylpiperidine,
3-methylpiperidine,
4-methylpiperidine,
N-methylpiperazine,
  1-methylhomopiperazine,
  1-acetylpiperazine,
  N-carboethoxypiperazine,
  3-methylpiperazine-2-carboxylic acid,
  2-methylpiperazine,
  2,3,5,6,-tetramethylpiperazine,
  1,4-dimethylpiperazine,
  2,6-dimethylpiperazine,
  2-methyl-1-phenylpiperazine,
  1-(1-phenylethyl)piperazine,
  1-(2-pyrazinyl)piperazine,
  1-cyclopropylpiperazine,
  1-cyclobutylpiperazine,
  1,2,3,4-tetrahydroisoquinoline,
  imidazole,
  homopiperdine, or pharmaceutically acceptable salts and hydrates thereof.

Examples of —O($CH_2$)p(N-methylpiperdin-3-yl) include:
(2-(N-methylpiperdin-3-yl)ethyl)oxy,
(3-(N-methylpiperdin-3-yl)propy)loxy,
(4-(N-methylpiperdin-3-yl)butyl)oxy.

Examples of —O—($CH_2$)p$NR_9R_{10}$ include:
(2-(1-piperidinyl)ethyl)oxy,
(2-(4-morpholinyl)ethyl)oxy,
(2-(1-pyrrolidinyl)ethyl)oxy,
(3-(N-methylpiperazinyl)propyl)oxy,
(4-(N-ethyl-N-phenylamino)butyl)oxy,
(5-(diethylamino)pentyl)oxy,
(2-(4-benzylpiperazinyl)ethyl)oxy, and
(3-(N,N-diisopropyl)propyl)oxy.

Examples of O—($CH_2$)p$OR_{15}$ include:
(2-methoxyethyl)oxy,
(3-butoxypropyl)oxy,
(4-phenoxybutyl)oxy,
(2-benzyloxyethyl)oxy,
(2-(2-(1-piperidinyl)ethoxy)ethyl)oxy, and
(3-(3-picolylmethoxy)propyl)oxy.

Examples of —($CH_2$)$_n$pyridinyl include:
2-pyridyl,
3-pyridylmethyl, and
4-pyridylethyl.

Examples of —($CH_2$)$_n$piperdinyl include:
1-piperidinyl,
1-peiperidinylmethyl,
2-(1-piperidinyl)ethyl, and
3-(1-piperidinyl)propyl.

Examples of —($CH_2$)$_q$$NR_9R_{10}$ include:
(1-piperidinyl)methyl,
2-(4-morpholinyl)ethyl,
3-(1-pyrrolindinyl)propyl, and
4-(1-piperazinyl)butyl.

Examples of —($CH_2$)$_n$C(O)—($CH_2$)$_n$$R_9$ include:
acetyl, acetylmethyl, methylacetylmethyl, methylacetylethyl, phenylacetyl, phenylacetylmethyl,
2-(phenylacetyl)ethyl,
2-pyridylacetyl,
3-pyridylacetylmethyl,
3-(t-butylacetyl)propyl, and
4-(ethylacetyl)butyl.

Examples of —($CH_2$)$_n$C(O)O—($CH_2$)$_n$$R_9$ include:
carbomethoxy,
carbomethoxymethyl,
2-(carbomethoxy)ethyl,
carbophenylmethoxy,
carbophenylmethoxymethyl,
2-(carbo(3-pyridyl)methoxy)ethyl,
carboethoxymethyl, and
3-(carbopropoxy)propoxy.

Examples of —($CH_2$)$_n$C(O)O—($CH_2$)$_p$$NR_9R_{10}$ include:
—C(O)O—($CH_2$)$_2$N(ethyl)$_2$,
—($CH_2$)C(O)O—($CH_2$)$_2$N($CH_3$)(phenyl),
—($CH_2$)$_3$C(O)O—($CH_2$)$_3$(1-pyrrolidine),
—($CH_2$)$_3$C(O)O—($CH_2$)$_2$(1-piperidinyl), and
—($CH_2$)C(O)O—($CH_2$)$_2$(4-morpholinyl).

Examples of —($CH_2$)$_n$C(O)($CH_2$)$_n$$NR_9R_{10}$ include:
—($CH_2$)C(O)($CH_2$)N(ethyl)$_2$,
—($CH_2$)$_2$C(O)($CH_2$)$_2$N(methyl)(phenyl),
—C(O)(1-pyrrolidine),
—($CH_2$)$_2$C(O)($CH_2$)$_3$(1-piperidine), and
—($CH_2$)$_3$C(O)($CH_2$)(4-morpholine).

Examples of —O—($CH_2$)$_n$C(O)—($CH_2$)$_n$$R_9$ include:
—O—($CH_2$)C(O)—($CH_2$)($CH_3$),
—O—C(O)—($CH_2$)$_2$($CH_3$),
—O—($CH_2$)$_3$C(O)—($CH_2$)phenyl,
—O—($CH_2$)$_2$C(O)—($CH_2$)$_3$(2-pyridyl),
—O—($CH_2$)C(O)—($CH_2$)$_2$(3-pyridyl), and
—O—($CH_2$)$_4$C(O)—($CH_2$)$_4$(t-butyl).

Examples of —O—($CH_2$)$_n$C(O)O—($CH_2$)$_n$$R_9$ include:
—O—($CH_2$)C(O)O—($CH_2$)($CH_3$),
—O—C(O)O—($CH_2$)$_2$($CH_3$),
—O—($CH_2$)$_2$C(O)O—($CH_2$)$_3$(phenyl), and
—O—($CH_2$)$_3$C(O)O—($CH_2$)$_2$(3-pyridyl).

Examples of —O—($CH_2$)$_n$C(O)—($CH_2$)$_n$$NR_9R_{10}$ include:
—O—($CH_2$)C(O)—($CH_2$)N($CH_3$)$_2$,
—O—C(O)—($CH_2$)(1-pyrrolidine), —O—(CH$_2$)C(O)—(1-piperidine),
—O—(CH$_2$)$_2$C(O)—(CH$_2$)(1-N-methylpiperazine),
—O—(CH$_2$)$_2$C(O)—(CH$_2$)$_2$(4-morpholine),
—O—(CH$_2$)$_2$C(O)—(CH$_2$)$_3$(cyclohexylamine),
—O—(CH$_2$)$_2$C(O)—(CH$_2$)$_3$(t-butylamine),
—O—(CH$_2$)C(O)—(CH$_2$)$_2$(1-phenylethylamine),
—O—(CH$_2$)C(O)—(CH$_2$)$_2$(aniline),
—O—(CH$_2$)C(O)—(CH$_2$)(L-phenylalanine ethyl ester), and
—O—(CH$_2$)$_2$nC(O)—(CH$_2$)$_3$(3-pyridylamine).

Examples of —N(R$_9$)(CH$_2$)$_n$C(O)—(CH$_2$)$_n$R$_{10}$ include:
—N(CH$_3$)C(O)—(CH$_3$),
—N(H)(CH$_2$)$_2$C(O)—(CH$_2$)(phenyl),
—N(H)(CH$_2$)C(O)—(CH$_2$)$_2$(3-pyridyl), and
—N(CH$_3$)(CH$_2$)$_3$C(O)—(CH$_2$)(CH$_3$).

Examples of —N(R$_9$)—(CH$_2$)$_n$C(O)O—(CH$_2$)$_n$R$_{10}$ include:
—N(H)—(CH$_2$)C(O)O—(CH$_3$),
—N(H)—(CH$_2$)$_2$C(O)O—(CH$_2$)(benzyl),
—N(H)—(CH$_2$)$_2$C(O)O—(CH$_2$)(3-pyridyl), and
—N(CH$_3$)—(CH$_2$)C(O)O—(CH$_2$)$_2$(t-butyl).

Examples of —N(R$_9$)(CH$_2$)$_n$C(O)—(CH$_2$)$_n$NR$_9$R$_{10}$ include:
—N(H)(CH$_2$)C(O)—(CH$_2$)N(CH$_3$)$_2$,
—N(H)C(O)—(CH$_2$)(1-pyrrolidine),
—N(H)(CH$_2$)$_2$C(O)—(CH$_2$)$_2$(1-piperidine), and
—N(CH$_3$)(CH$_2$)C(O)—(CH$_2$)$_2$(4-morpholine).

Examples of —O—(CH$_2$)$_n$phenyl include:
2-(4-trifluoromethylphenyl)ethoxy,
4-chlorophenoxy,
4-fluorophenylmethoxy,
3-(4-methoxyphenyl)propoxy,
4-(2-methyl-4-fluorophenyl)butoxy,
2-(2-methoxyphenyl)ethoxy,
3-methoxyphenylmethoxy,
4-carbomethoxyphenylmethoxy,
2-(3,4-dichlorophenyl)ethoxy,
4-ethoxyphenylmethoxy,
3-(4-nitrophenyl)propoxy,
4-t-butylphenylmethoxy,
4-benzyloxyphenylmethoxy, and
2-(3-trifluoromethylphenyl)ethoxy.

Examples of —O—(CH$_2$)$_n$pyridine include:
2-pyridyloxy,
3-pyridylmethoxy, and
2-(4-pyridyl)ethoxy.

Examples of —O(CH$_2$)$_n$C(O)—(CH$_2$)$_n$pyridine include:
—O(CH$_2$)C(O)—(CH$_2$)(2-pyridine),
—O(CH$_2$)$_3$C(O)—(CH$_2$)(3-pyridine), and
—O(CH$_2$)$_2$C(O)—(CH$_2$)$_3$(4-pyridine).

Examples of —O—(CH$_2$)$_n$C(O)O—(CH$_2$)$_n$pyridine include:
—O(CH$_2$)C(O)O—(CH$_2$)(2-pyridine),
—O(CH$_2$)$_3$C(O)O—(CH$_2$)(3-pyridine), and
—O(CH$_2$)$_2$C(O)O—(CH$_2$)$_3$(4-pyridine).

Examples of —O(CH$_2$)$_n$C(O)—N(R$_9$)(CH$_2$)$_n$pyridine include:
—O(CH$_2$)C(O)—N(CH$_3$)(CH$_2$)(2-pyridine),
—O(CH$_2$)$_2$C(O)—N(CH$_3$)(CH$_2$)(3-pyridine), and
—O(CH$_2$)C(O)—N(benzyl)(CH$_2$)$_2$(4-pyridine).

Examples of —O—(CH$_2$)$_n$quinoxalinyl include:
2-quinoxalinyloxy,
2-quinoxalinylmethoxy, and
2-(2-quinoxalinyl)ethoxy.

Examples of —O—(CH$_2$)$_n$quinolinyl include:
2-quinolinyloxy,
2-quinolinylmethoxy, and
2-(2-quinolinyl)ethoxy.

Examples of —O—(CH$_2$)$_n$pyrazinyl include:
2-pyrazinyloxy,
2-pyrazinylmethoxy, and
2-(2-pyrazinyl)ethoxy.

Examples of —O—(CH$_2$)$_n$naphthyl include:
1-naphthyloxy,
2-naphthylmethoxy, and
2-(1-naphthyl)ethoxy.

Examples of —O—(CH$_2$)$_n$C(O)—(CH$_2$)$_n$naphthyl include:
—O—(CH$_2$)C(O)—(CH$_2$)(1-naphthyl),
—O—(CH$_2$)$_2$C(O)—(CH$_2$)(2-naphthyl),
—O—C(O)—(CH$_2$)(1-naphthyl), and
—O—(CH$_2$)2C(O)—(CH$_2$)$_2$(2-naphthyl).

Examples of —O—(CH$_2$)$_n$C(O)O—(CH$_2$)$_n$naphthyl include:
—O—(CH$_2$)C(O)O—(CH$_2$)(1-naphthyl),
—O—(CH$_2$)$_2$C(O)O—(CH$_2$)(2-naphthyl),
—O—C(O)O—(CH$_2$)(1-naphthyl), and
—O—(CH$_2$)2C(O)O—(CH$_2$)$_2$(2-naphthyl).

Examples of —O—(CH$_2$)$_n$C(O)NR$_9$—(CH$_2$)$_n$naphthyl include:
—O—(CH$_2$)C(O)N(H)(CH$_2$)(1-naphthyl),
—O—(CH$_2$)C(O)N(CH$_3$)(CH$_2$)$_2$(2-naphthyl), and
—O—(CH$_2$)C(O)N(benzyl)(CH$_2$)$_3$(1-naphthyl).

Examples of —(CH$_2$)$_q$—OH include: hydroxymethyl, hydroxyethyl and hydroxybutyl.

Examples of (CH$_2$)$_q$OC(O)R$_9$ include:
(CH$_2$)OC(O)methyl,
(CH$_2$)$_2$OC(O)ethyl,
(CH$_2$)$_3$OC(O)phenyl,
(CH$_2$)$_4$OC(O)(3-pyridyl), and
(CH$_2$)OC(O)thiophene.

Examples of —(CH$_2$)$_q$OC(O)—NR$_9$R$_{10}$ include:
—(CH$_2$)OC(O)—N(CH$_2$)$_2$,
—(CH$_2$)$_2$OC(O)—N(ethyl)$_2$,
—(CH$_2$)$_3$OC(O)—(1-pyrrolidine),
—(CH$_2$)$_4$OC(O)—(1-piperidine), and
—(CH$_2$)OC(O)—N-benzylamine.

Examples of -(1-cyclohexyl-1H-tetrazol-5-yl)C$_1$–C$_4$ alkoxy, -(1-(C$_1$–C$_5$ alkyl)-1H-tetrazol-5-yl)C$_1$–C$_4$ alkoxy include:
-(1-cyclohexyl-1H-tetrazol-5-yl)methoxy,
-(1-cyclohexyl-1H-tetrazol-5-yl)ethoxy,
-(1-(methyl)-1H-tetrazol-5-yl)methoxy,
-(1-(cyclopropyl)-1H-tetrazol-5-yl)ethoxy,
-(1-(1-tert-butyl)-1H-tetrazol-5-yl)propoxy, and
-(1-(cyclopenyl)-1H-tetrazol-5-yl)methoxy.

Examples of -(1-(phenyl)-1H-tetrazol-5-yl)C$_1$–C$_4$ alkoxy (wherein phenyl is optionally substituted with one, 2 or 3 C$_1$–C$_4$ alkyl, C$_1$–C$_4$ alkoxy, halo or trifluoromethyl) include:
-(1-(phenyl)-1H-tetrazol-5-yl)methoxy,
-(1-(phenyl)-1H-tetrazol-5-yl)ethoxy,
-(1-(4-methoxyphenyl)-1H-tetrazol-5-yl)methoxy, and
-(1-(4-fluorophenyl)-1H-tetrazol-5-yl)propoxy.

Examples of -(1-(pyridinyl)-1H-tetrazol-5-yl)C$_1$–C$_4$ alkoxy or -(1-(1-phenylethyl)-1H-tetrazol-5-yl)C$_1$–C$_4$ alkoxy include:
-(1-(2-pyridinyl)-1H-tetrazol-5-yl)methoxy,
-(1-(3-pyridinyl)-1H-tetrazol-5-yl)ethoxy,
-(1-(4-pyridinyl)-1H-tetrazol-5-yl)propoxy,
-(1-(1-phenylethyl)-1H-tetrazol-5-yl)methoxy, and
-(1-(1-phenylethyl)-1H-tetrazol-5-yl)ethoxy.

The tertiary amines and aromatic heterocyclic amines of the subject specification and claims include the N-oxides thereof.

Pharmaceutically acceptable salts means salts useful for administering the compounds of this invention and include hydrochloride, hydrobromide, hydroiodide, sulfate, phosphate, acetate, propionate, lactate, mesylate, maleate malate, succinate, tartrate, citric acid and the like. These salts may be in hydrated form.

Various compounds of Formula I are potent inhibitors of cell proliferation and are contemplated as useful in the treatment of proliferative diseases such as cancer, rheumatoid arthritis, psoriasis, pulmonary fibrosis, scleroderma, cirrhosis of the liver and for the improved utilization of artificial prosthetic devices such as arterial grafts. These agents may also be useful in the prevention of treatment of obstruction or restenosis of arteries by subsequent administration of drug in cases such as by-pass surgery, coronary by-pass surgery, balloon angioplasty (and other procedures directed at re-establishing patency in occluded or partly occluded vessels, i.e. atherectomy, laser or ultrasonic procedures), transplants, and post-thrombotic re-stenosis.

The compounds of Formula I are active as inhibitors of cell proliferation as shown in Table 1 by the test procedure described in Pledger W. J., Stiles C. D., Antniades H. N., Scher C. D., (Proc. Natl. Acad. Sci (USA) (1977). In addition, various compounds of Formula I are also inhibitors of ADP induced platelet aggregation and are useful in the prevention or treatment of thrombotic diseases and related complications by, for example, inhibition or reversal of platelet aggregation, or platelet adhesion or blood coagulation.

Most compounds of Formula I are active as inhibitors of platelet aggregation as shown in Table 1 by the test procedure described in Born, G. R., Cross M. J., J. Physiol., 168, p. 178 (1963).

Accordingly, in using compounds of Formula I for the prevention or treatment of atherosclerotic disease or thrombotic diseases, an oral route of administration, either by conventional oral dosage forms or by mixture with food, represents the preferred method of their systemic administration. Alternatively, however, these compounds may be administered by other convenient routes of administration whereby systemic activity is obtained. These other routes of administration would include rectal, vaginal, subcutaneous, intramuscular, intravenous, and like routes.

In using compounds of Formula I for use in angioplasty, an oral route of administration represents the preferred method of their systemic administration. Alternatively, however, these compounds may be administered by other convenient routes of administration whereby systemic activity is obtained.

The patient or animal being treated must be given periodic doses of the drug in amounts effective to reduce serum and/or arterial cholesterol, and reduce arterial atherosclerotic lesion size (as determined by angiogram, ultrasound, NMR, etc.); or, by the inhibition or reversal of platelet aggregation, platelet adhesion or blood coagulation; or, by preventing arterial occlusion in vascular trauma associated with procedures such as by-pass grafts, coronary by-passes, angioplasty, post-thrombotic re-stenosis and transplants.

Such effective dosages are readily determined by methods known in the art. For example, small daily doses of the drug (e.g., 0.01–200 mg/kg) may be administered initially with higher succeeding doses until levels of serum and/or arterial cholesterol are favorably affected. By this regimen, a compound of Formula I is administered initially at doses as low as about 0.01 mg/kg per patient per day, with increasing doses up to about 200 mg/kg per patient per day. In the event the antiatherogenic response in a patient being treated at a dose of 200 mg/kg per day is insufficient, higher doses are also utilized to the extent patient tolerance permits further increases in dose.

While the preferred dosage regimen is with single daily dosing of patients, also preferred for obtaining more uniform serum levels of drug are multiple dosages per day (e.g., up to 4–6 times daily). Accordingly, when 4 daily doses of drug are to be administered, each such dose may be about 50 mg/kg per patient per dose, or higher depending on tolerance.

Similar doses are employed in hon-human mammals, e.g. 0.01–200 mg/kg/day.

The compounds of the subject invention can be prepared as shown in the four Schemes, below. In the first Scheme I, benzoylacetone was treated with boron trifluoride etherate to provide an 82% yield of the corresponding complex. Treatment of this complex with 4-morpholine dichloromethylene iminium chloride afforded a 2.5% yield of the desired compound along with an equivalent recovery of carboxamide byproduct.

This same chemistry can be applied using 4'-acetyloxyacetophenone. Formation of the boron difluoride complex (43%) followed by treatment with 4-morpholine dichloromethylene iminium chloride gives a mixture of byproduct and the desired compound (as an equimolar mixture of the acetates and the corresponding phenols).

In Scheme II, the intermediate compound is prepared by the coupling of lithio acetoxymorpholine and ethyl phenylpropiolate in 27% yield (unoptimized). Cyclization is then accomplished with trifluoroacetic acid to afford the subject compounds in about a 69% yield. The ready availability of phenylpropiolates and acetoxyamines (two steps from the corresponding benzaldehyde) makes this a general method for the synthesis of 6-aryl-2-amino-4-pyrones.

Compounds of the subject invention can also be prepared by a another means of synthesis, generally following Scheme II. For example, 4-Phenylmethoxybenzaldehyde is reacted with carbon tetrabromide and triphenylphosphine to afford dibromoolefin which upon treatment with n-butyl lithium and methyl chloroformate gave the phenyl propiolate.

Reaction of the first compound with lithioacetoxymorpholine affords the product in an 81% yield. Optimal cyclization conditions for the product were found to be 15% trifluoroacetic acid in methylene chloride producing the aminopyrone in 72% yield. In some situations the use of trifluoroacetic acid as solvent is required to afford proper product in sufficiently high yields.

In yet another approach to prepare compounds of the subject invention, Scheme III begins with a phenyl propiolate reacted with acetyl-methylphenyl sulfoxide to produce the desired intermediate compound. The intermediate is then warmed in methanol to yield the desired 4-pyrone. Pummerer rearrangement with acetic anhydride at 110° C. gives an intermediate which is reduced ($NaBH_4$) to an alcohol which is tosylated (TSCl) to give a tosylate. The tosylate is displaced with an amine to yield the subject compound 6-phenyl-2-methylamino-4-pyrone.

The foregoing Schemes provide a general explanation of successful procedures for preparing the subject compounds which are described in further detail in the individual examples.

The compounds of the invention were tested for biological activity and the individual results are reported in Table 1, Biological Data. The data collected shows the antiprolifeative assay results measured in EC50 (uM) and percent inhibition at the maximum concentration tested. Only Compound 14 exhibited no measurable antiproliferation or inhibition activity but still a novel compound. Also, reported is the percent inhibition of platelet aggregation at 10 ug/ml and 30 ug/ml concentrations.

Typical examples of the subject compounds are identified by structure in Table 2, below.

TABLE 1

| | Biological Data | | | |
|---|---|---|---|---|
| | Antiproliferative Assay Data | | Inhibition of Platelet Aggregation | |
| Compound | EC50 ($\mu$M) | Inhibition (%) | 10 $\mu$g/ml | 30 $\mu$g/ml |
| 1 | 29.4 | 54 | 75 | 95 |
| 2 | 6.9 | — | 10 | 15 |
| 3 | 28.0 | — | 45 | 50 |
| 4 | 9.4 | 66 | 45 | 60 |
| 5 | 11.2 | 77 | 40 | 55 |
| 6 | 14.8 | 72 | 25 | 40 |
| 7 | >31.2 | 30 | 60 | 70 |
| 8 | 6.8 | — | 35 | 35 |
| 9 | 11.6 | 88 | 60 | 65 |
| 10 | 62.2 | 34 | — | — |
| 11 | 22.9 | — | 10 | 10 |
| 12 | 41 | 36 | 0 | 0 |
| 13 | — | 20 | 0 | 0 |
| 14 | — | 0 | 0 | 0 |
| 15 | 9.1 | 96 | 0 | 0 |
| 16 | 28.5 | 73 | 5 | 44 |
| 17 | — | 20 | 0 | 0 |
| 18 | — | 8 | 10 | 18 |
| 19 | — | 12 | 5 | 10 |
| 20 | — | 9 | 0 | 20 |
| 21 | — | 13 | 10 | 10 |
| 22 | >20 | 25 | 42 | 61 |
| 23 | 0.25 | — | 20 | 50 |
| 24 | 0.48 | — | 10 | 50 |
| 25 | 18.7 | — | 45 | 55 |

TABLE 2

| | | | | | Compound Identification | | |
|---|---|---|---|---|---|---|---|
| Compound | X | Y | $R_1$ | $R_2$ | $R_3$ | $R_4$ | $R_5$ |
| 1 | H | 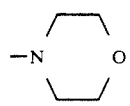 | H | H | OH | H | H |
| 2 | H | 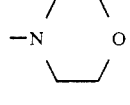 | H | H | 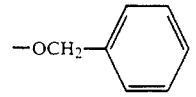 | H | H |
| 3 | H | 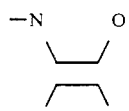 | H | H | H | H | H |
| 4 | H | 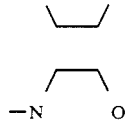 | H | H | —OCH$_2$COt—Bu | H | H |
| 5 | H | 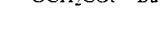 | H | H | 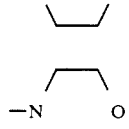 | H | H |
| 6 | H | 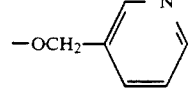 | H | H | 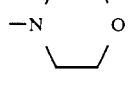 | H | H |
| 7 | H | 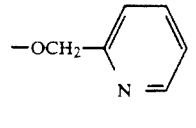 | H | H | 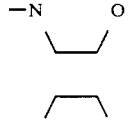 | H | H |
| 8 | H | 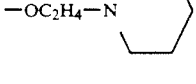 | H | H | 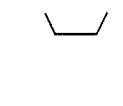 | H | H |

TABLE 2-continued

| Compound | X | Y | R₁ | R₂ | R₃ | R₄ | R₅ |
|---|---|---|---|---|---|---|---|
| 9 | H | −N(morpholine) | H | H | H | H | −OCH₂Ph |
| 10 | H | −N(morpholine) | H | H | H | H | OH |
| 11 | H | −N(morpholine) | H | H | −OCH(nBu)Ph | H | H |
| 12 | H | −CH₂−N(morpholine) | H | H | −OCH₂Ph | H | H |
| 13 | H | −CH₂−N(piperidine) | H | H | −OCH₂Ph | H | H |
| 14 | H | −CH₂−N(morpholine) | H | H | −OH | H | H |
| 15 | H | −N(morpholine) | H | H | H | −OCH₂Ph | H |
| 16 | H | −N(morpholine) | H | H | H | −OH | H |
| 17 | H | −N(morpholine) | H | H | −CH₂−OH | H | H |
| 18 | H | −N(morpholine) | H | H | −CH₂−N(piperidine) | H | H |
| 19 | H | −N(morpholine) | H | H | −CH₂−N(pyrrolidine) | H | H |
| 20 | H | −N(morpholine) | H | H | −CH₂−N(N−CH₃ piperazine) | H | H |
| 21 | H | −N(morpholine) | H | H | −CH₂−N(piperidine-CH₂OH) | H | H |

TABLE 2-continued

| Compound | X | Y | R₁ | R₂ | R₃ | R₄ | R₅ |
|---|---|---|---|---|---|---|---|
| 22 | H | —N(CH₂CH₂)₂O (morpholinyl) | H | H | —F | H | H |
| 23 | H | —N(CH₂CH₂)₂O (morpholinyl) | H | H | —N(CH₂CH₂)₂ (pyrrolidinyl) | H | H |
| 24 | H | —N(CH₂CH₂)₂O (morpholinyl) | H | H | —N(CH₂CH₂)₂CH₂ (piperidinyl) | H | H |
| 25 | H | —N(CH₂CH₂)₂O (morpholinyl) | H | H | —NH₂ | H | H |

EXAMPLE 1

2-(4-Hydroxyphenyl)-6-(4-morpholinyl)-4H-pyran-4-one (Compound 1)

4'-Hydroxyacetophenone (10 g, 73.4 mmole) was suspended in 200 ml dichloromethane in a 500 ml one neck round bottom flask under nitrogen at 0° C. The suspension was treated with diisopropylethylamine (14.7 ml, 84.5 mmole) followed by acetyl chloride (6.0 ml, 84.5 mmole) in 1×50 ml dichloromethane slowly dropwise. The reaction mixture was stirred 30 minutes at 0° C. and then for 1 hour at room temperature. The mixture was washed with 1×100 ml 10% hydrochloric acid and the organics were dried over magnesium sulfate. The dried organics were concentrated in vacuo to a yellow oil. The oil was distilled via kugelrohr (high vacuum, 165° C.) to give 12.25 g (94%) of 4'-acetoxy-acetophenone as a white solid. Melting Point: 47°–49° C. 4'-Acetoxy-acetophenone (10 g, 56.2 mmole) was dissolved in acetic anhydride (10.6 ml, 112.2 mmole) in an oven dried 50 ml two neck round bottom flask under nitrogen. The solution was cooled to 0° C. and boron trifuoride gas was bubbled into the reaction mixture until it was saturated. The reaction was stirred 1 hour at room temperature and was poured into 600 ml diethyl ether. The orange precipitate was collected, washed with fresh diethyl ether, and was dried to afford 6.6 g (43%) of a boron difluoride complex. Melting Point: 130°–132° C.

The 4'-Acetoxy-benzoylacetone-boron difluoride complex (4.02 g, 15 mmole) was combined with 4-morpholine phosgeniminium chloride (3.7 g, 18 mmole) in 50 ml 1,2-dichloroethane in a 100 ml one neck round bottom flask under nitrogen. The reaction mixture was heated to 80° C. for 6 hours and was cooled to room temperature. The dichloroethane was removed in vacuo and the residue was dissolved in 50 ml acetonitrile in a 100 ml one neck round bottom flask. The solution was diluted with 5 ml water and the reaction mixture was stirred overnight at room temperature. The acetonitrile was removed in vacuo and the aqueous residue was diluted with 30 ml methanol and 15 ml 2N sodium hydroxide. The reaction mixture was stirred for 3 hours at room temperature. The methanol was removed in vacuo and the pH of the aqueous residue was adjusted to 5 with 10% hydrochloric acid (pH meter). The mixture was extracted with 4×25 ml dichloromethane followed by 4×20 ml dichloromethane. The combined organics were dried over magnesium sulfate and were concentrated in vacuo to a semisolid residue.

The crude material was chromatographed over 68 g silica gel (230–400 mesh) eluting with 60–80% acetone-/ethyl acetate for the first 144 fractions while collecting 9 ml fractions. Fractions 141–213 were combined and concentrated to afford 281 mg (4.9%) of 3-carboxamido-pyrone as a tan solid. Fractions 276–302 were eluted with 80% acetone/ethyl acetate + 5% methanol and were combined and concentrated to afford 100 mg (2.4%) of Compound 1 as an off white solid.

H-NMR (CDCl3,TMS): d 3.43(m,4H,CH2); 3.84(m,4H,CH2); 5.42(d,J=2 Hz,1H,CH); 6.42(d,J=2 Hz,1H,CH); 6.94(d,2H,ArH); 7.53(d,2H,ArH); 9.41(bs,1H,OH) ppm.

TLC (silica gel-60, F-254): Rf=0.26, 10% methanol/-dichloromethane.

Melting Point: >250° C.

Infrared (v max, mineral oil): 2926, 2602, 1649, 1549, 1508, 1450, 1425, 1248, 1174, 841 cm-1.

Mass Spectrum: Calculated for C15H15NO4: 273.1001, Found: 273.1004.

EXAMPLE 2

2-(4-Morpholinyl)-6-(4-(phenylmethoxy)phenyl)-4H-pyran-4-one (Compound 2)

2-Morpholinyl-6-(4-hydroxyphenyl)-4-pyrone(85 mg, 0.31 mmole), as prepared in Example 1, was suspended in 5 ml acetonitrile in a 25 ml one neck round bottom flask under nitrogen. The suspension was treated successively with potassium carbonate (249 mg, 1.8 mmole) and benzyl bromide (0.050 ml, 0.42 mmole). The reaction mixture was stirred at 65° C. for 4 hours. The reaction was cooled to room temperature and the acetonitrile was removed in vacuo. The residue was washed with 1×25 ml dichloromethane and the insoluble material was removed by filtration. The filtrate was concentrated in vacuo to a yellow solid.

The solid was chromatographed over 6 g silica gel (230–400 mesh) eluting with 3% methanol/dichloromethane and collecting 3 ml fractions. Fractions 12–18 were combined and concentrated to afford 74 mg (66%) of Compound 2 as a pale yellow solid.

H-NMR (CDCl3,TMS): d 3.42(m,4H,CH2); 3.84(m,4H,CH2); 5.13(s,2H,CH2); 5.42(d,J=2 Hz,1H,CH); 6.46(d,J=2 Hz,1H,CH); 7.04(d,2H,ArH); 7.26–7.45(m,5H,ArH); 7.60(d,2H,ArH) ppm.

NMR (CDCl3): d 44.92; 65.93; 70.19; 90.48; 108.22; 115.37; 124.02; 127.06; 127.45; 128.26; 128.73; 136.23; 159.21; 160.88; 163.37; 180.34 ppm.

TLC (silica gel-60, F-254): Rf=0.35, 10% methanol/dichloromethane.

Melting Point: 202.5°–203.5° C.

Infrared (v max, mineral oil): 2925, 1647, 1600, 1564, 1512, 1406, 1258, 1221, 1119 cm-1.

Ultraviolet (v max, ethanol): 227, 257, 287, 299, 322 nm.

Mass Spectrum: Calculated for C22H21NO4: 363.1470 Found: 363.1476.

EXAMPLE 3

2-(4-Morpholinyl)-6-phenyl-4H-pyran-4-one (Compound 3)

A flame dried 500 ml three neck round bottom flask under nitrogen was charged with 140 ml dry tetrahydrofuran and diisopropylamine (23.9 ml, 170.3 mmole). The solution was cooled to 0° C., was treated with butyllithium (115 ml, 178.7 mmole), and was stirred 30 minutes. The mixture was treated with acetyl morpholine (9 ml, 77.4 mmole) in 30 ml dry tetrahydrofuran and the reaction was stirred 30 minutes at 0° C. Ethylphenyl propiolate (12.8 ml 77.4 mmole) in 30 ml dry tetrahydrofuran was added slowly dropwise to the reaction mixture at 0° C. The reaction was stirred 3 hours at 0° C. and was quenched with 30 ml water. The yellow precipitate was collected and washed successively with water, methanol, and diethyl ether to afford 5.4 g (27%) of acetylenic ketoamide. Melting Point: >300° C.

Acetylenic ketoamide (760 mg, 2.95 mmole) was dissolved in 10 ml trifluoroacetic acid in a 50 ml one neck round bottom flask under nitrogen. The reaction mixture was warmed to 60° C. for 20 hours and was cooled to room temperature. The trifluoracetic acid was removed in vacuo and the residue was diluted with 20 ml dichloromethane. The mixture was extracted with 1×20 ml 1:1 saturated sodium chloride/2N sodium hydroxide. The aqueous layer was back extracted with 3×20 ml dichloromethane. The combined organics were dried over magnesium sulfate and were concentrated in vacuo to a dark brown semisolid residue.

The residue was chromatographed over 68 g silica gel (230–400 mesh) eluting with 3% methanol/dichloromethane and collecting 12 ml fractions. Fractions 27–36 were combined and concentrated to afford 525 mg (69%) of Compound 3 as a tan solid.

H-NMR (CDCl3,TMS): d 3.44(m,4H,CH2); 3.84(m,4H,CH2); 5.46(d,J=2 Hz,1H,CH); 6.54(d,J=2 Hz,1H,CH); 7.45–7.50(m,3H,ArH); 7.62–7.69(m,2-H,ArH) ppm.

C-NMR (CDCl3): d 44.66; 65.70; 90.32; 109.30; 125.23; 128.89; 130.75; 131.13; 158.95; 163.25; 179.88 ppm.

TLC (silica gel-60, F-254): Rf=0.46, 10% methanol/dichloromethane.

Melting Point: 136.5°–137.5° C.

Infrared (v max, mineral oil): 2926, 1651, 1601, 1578, 1565, 1402, 1229, 1029, 792 cm-1.

Mass Spectrum: Calculated for C15H15NO3: 257.1052, Found: 257.1053.

Analysis: Calculated for C15H15NO3: C,70.02; H,5.88; N,5.44; Found: C,69.99; H,5.74; N,5.59.

EXAMPLE 4

2-(4-Morpholinyl-6-(4-(phenylmethoxy)phenyl)-4H-pyran-4-one (Compound 2)

Carbon tetrabromide (78.1 g, 235.6 mmole) and triphenylphosphine (123.5 g, 471.2 mmole) were combined in 460 ml dichloromethane in a flame dried 1000 ml three neck round bottom flask under nitrogen at 0° C. The mixture was stirred 1 hour at 0° C. and was treated portionwise with 4-benzyloxybenzaldehyde (25 g, 117.8 mmole). The reaction was stirred 30 minutes at 0° C. and was washed successively with 1×100 ml water and 1×100 ml saturated sodium chloride. The organics were dried over magnesium sulfate and were poured into 3 liters hexane. The supernatant was collected and the residue was dissolved in a minimum amount of dichloromethane. This solution was also poured into 3 liters hexane and the process was repeated one more time. The combined supernatants were filtered through a 125 ml plug of silica gel (230–400 mesh) in a 600 ml coarse filter funnel. The plug was washed with 1 liter 15% ethyl acetate/hexane and the combined eluents were concentrated in vacuo to provide 38.2 g (89%) of 2-(4-Benzyloxyphenyl)-1,1-dibromo-ethene as a white solid. Melting Point: 97°–98° C. The dibromoolefin (20 g, 54.3 mmole) was dissolved in 200 ml dry tetrahydrofuran in a flame dried 500 ml three neck round bottom flask under nitrogen. The solution was cooled to −78° C. and was treated slowly dropwise with butyllithium (70 ml, 108.6 mmole). The reaction was stirred 1 h at −78° C. followed by 1 hour at 0° C. The mixture was cooled to −78° C. and was treated with methyl-chloroformate (4.6 ml, 60 mmole). The reaction mixture was stirred for 20 minutes at −78° C. and then for 1.5 hours at 0° C. The reaction was quenched with 1×100 ml 1:1 saturated ammonium chloride/saturated sodium chloride. The layers were separated and the aqueous layer was washed with 2×100 ml diethyl ether. The combined organics were dried over magnesium sulfate and were concentrated in vacuo to a red oil. The oil was crystallized and then recrystallized from hexane to provide 9.2 g (75%) of methyl-4-benzyloxyphenyl-propiolate as orange tinged flakes. Melting Point: 78° C.

Acetyl morpholine (3.99 ml, 34.5 mmole) was dissolved in 30 ml dry tetrahydrofuran in an oven dried 100 ml two neck round bottom flask under nitrogen. The solution was cooled to 0° C. and was treated slowly dropwise with lithium diisopropylamide (23 ml, 34.5 mmole). The reaction mixture was stirred 30 minutes at 0° C. and was susequently added slowly dropwise via cannula to a solution of the previously prepared propiolate (3.9 g, 17.2 mmole) in 40 ml dry tetrahydrofuran in a flame dried 250 ml three neck round bottom flask under nitrogen. The reaction was stirred 1 hour at 0° C. and was quenched with 100 ml water which resulted in the immediate solidification of the mixture. The mixture was diluted with water and the solid was collected. The solid was washed with diethyl ether and was dried to afford 5.06 g (81%) of acetylenic ketoamide (Morpholine-5-(4-benzyloxyphenyl)-3-oxo-pent-4-ynamide) as a pale yellow solid. Melting Point: 282°-285° C.

The acetylenic ketoamide just prepared (363 mg, 1.0 mmole) was suspended in 5 ml dichloromethane in a 25 ml one neck round bottom flask under nitrogen. The suspension was treated with 1 ml trifluoroacetic acid and was stirred 1.5 hour at room temperature. The mixture was diluted with 25 ml dichloromethane. The mixture was washed with 1×20 ml 2N sodium hydroxide and the organics were dried over magnesium sulfate. The organics were concentrated in vacuo to give 287 mg of a brown solid. The solid was recrystallized from ethyl acetate to afford 223 mg (61%) of Compound 2 as a pale solid.

H-NMR (CDCl3,TMS): d 3.41(m,4H,CH2); 3.83(m,4H,CH2); 5.12(s,2H,ArCH2); 5.42(d,J=2 Hz,1H,CH); 6.45(d,J=2 Hz,1H,CH); 7.03(d,2H,ArH); 7.30-7.45(m,5H,ArH); 7.60(d,2H,ArH) ppm. C-NMR (CDCl3): d 44.76; 65.79; 70.04; 90.32; 108.06; 115.23; 123.86; 126.91; 127.32; 128.12; 128.59; 136.09; 159.05; 160.73; 163.22; 180.14 ppm.

TLC (silica gel-60, F-254): Rf=0.28, 8% methanol/dichloromethane.

Melting Point: 205.4°-206° C.

Infrared (v max, mineral oil): 2925, 1647, 1600, 1564, 1512, 1406, 1252, 1230, 1119 cm-1.

Ultraviolet (v max, ethanol); 227, 256, 286, 299, 322 nm.

Mass Spectrum: Calculated for C22H21NO4: 363.1469, Found: 363.1470.

Analysis: Calculated for C22H21NO4: C,72.71; H,5.82; N,3.85. Found: C,72.53; H,5.99; N,3.90.

Following the general procedure of Example 4, but starting with the appropriate benzaldehyde, the following products can be prepared:

2-(4-morpholinyl)-6-(3-(phenylmethoxy)phenyl)-4H-pyran-4-one (Compound 15), mp 170.5°-171.5° C.;
2-(3-hydroxyphenyl)-6-(4-morpholinyl)-4H-pyran-4-one(Compound 16), mp 255.5°-256° C.

EXAMPLE 5

2-(4-Hydroxyphenyl)-6-(4-morpholinyl)-4H-pyran-4-one (Compound 1)

2-Morpholinyl-6-(4-benzyloxyphenyl)-4-pyrone (2.6 g, 7.15 mmole), which was prepared as in Example 4, was suspended in 50 ml methanol in a 100 ml one neck round bottom flask under nitrogen. The suspension was treated successively with 10% palladium on carbon (910 mg) and cyclohexene (3.9 ml, 38.5 mmole). The reaction mixture was heated at 60° C. for 1.5 hours and was filtered hot through a celite plug. The celite filter cake was washed well with 250 ml hot methanol. The filtrate was concentrated in vacuo to a crude solid. The solid was recrystallized from methanol to afford 1.6 g (82%) of Compound 1 as a white crystalline solid.

H-NMR (d6DMSO): d 3.38(m,4H,CH2); 3.71(m,4H,CH2); 5.36(d,J=2 Hz,1H,CH); 6.43(d,J=2 Hz,1H); 6.86(d,2H,ArH); 7.69(d,2H,ArH); 10.17(bs,1H,OH) ppm.

C-NMR (d6DMSO): d 46.14; 67.03; 90.94; 108.24; 117.55; 123.26; 128.91; 160.29; 161.71; 164.55; 180.29 ppm. TLC (silica gel-60, F-254): Rf=0.26, 10% methanol/dichloromethane.

Melting Point:>250° C.

Infrared (v max, mineral oil): 2925, 2537, 1647, 1612, 1564, 1511, 1447, 1425, 1246, 1174, 1120 cm-1.

Ultraviolet (v max, ethanol): 227, 257, 286, 298, 325 nm.

Mass Spectrum: Calculated for C15H15NO4: 273.1001, Found: 273.1000.

EXAMPLE 6

2-(4-(3,3-Dimethyl-2-oxobutoxy)phenyl)-6-(4-morpholinyl)-4H-pyran-4-one (Compound 4)

2-Morpholinyl-6-(4-hydroxyphenyl)-4-pyrone, as prepared in Example 5, (273 mg, 1.0 mmole) was suspended in 7 ml acetonitrile in a 25 ml one neck round bottom flask under nitrogen. The suspension was treated successively with potassium carbonate (829 mg, 6.0 mmole) and 1-bromo-3,3,3-trimethylacetone (336 ul, 2.5 mmole). The reaction mixture was heated at 60° C. for 6 hours and was cooled to room temperature. The acetonitrile was removed in vacuo and the residue was washed with 1×25 ml dichloromethane. The insoluble material was removed by filtration and the filtrate was concentrated in vacuo to a red oil.

The oil was chromatographed over 18 g silica gel (230-400 mesh) eluting with 3% methanol/dichloromethane and collecting 5 ml fractions. Fractions 28-42 were combined and concentrated to afford 144 mg of a purple solid. The solid was recrystallized from ethyl acetate to provide 125 mg (33%) of Compound 4 as a purple solid.

H-NMR (CDCl3,TMS): d 1.47(s,9H,CH3); 3.42(m,4H,CH2); 3.84(m,4H,CH2); 4.96(s,2H,CH2); 5.42(d,J=2 Hz,1H,CH); 6.44(d,J=2 Hz,1H,CH); 6.92(d,2H,ArH); 7.59(d,2H,ArH) ppm.

C-NMR (CDCl3): d 26.21; 43.06; 44.75; 65.78; 90.32; 114.95; 124.41; 126.93; 158.87; 160.01; 163.21; 180.06; 208.72 ppm. TLC (silica gel-60, F-254): Rf=0.53, 10% methanol/dichloromethane.

Melting Point: 181°-182.5° C.

Infrared (v max, mineral oil): 2925, 1720, 1644, 1605, 1566, 1508, 1408, 1234, 829 cm-1.

Ultraviolet (v max, ethanol): 226, 256, 286, 298, 321 mm.

Mass Spectrum: Calculated for C21H25NO5: 371.1733, Found: 371.1734

Analysis: Calculated for C21H25NO5: C,67.91; H,6.78; N,3.77. Found: C,67.57; H,6.91; N,3.84.

EXAMPLE 7

2-(4-Morpholinyl)-6-(4-(3-pyridinylmethoxy)phenyl)-4H-pyran-4-one (Compound 5)

2-Morpholinyl-6-(4-hydroxyphenyl)-4-pyrone, as prepared in Example 5, (273 mg, 1.0 mmole) was suspended in 6 ml dimethylformamide in a 25 ml one neck round bottom flask under nitrogen. The suspension was treated with sodium hydride suspension (192 mg, 4.0 mmole) and the reaction mixture was warmed to 60° C. for 40 minutes. The reaction was treated with 3-picolyl chloride hydrochloride (492 mg, 3.0 mmole) and the mixture was stirred 2 hours at 60° C. The reaction was poured into 50 ml 2N sodium hydroxide/ice and the mixture was extracted with 4×20 ml dichloromethane. The combined organics were washed with 4×25 ml 50% saturated sodium chloride and were dried over magnesium chloride. The dried organics were concentrated in vacuo to a yellow solid. The crude material was recrystallized twice from ethyl acetate to provide 229 mg (62%) of Compound 5 as a golden crystalline solid.

H-NMR (CDCl3,TMS): d 3.42(m,4H,CH2); 3.85(m,4H,CH2); 5.15(s,2H,ArCH2); 5.43(d,J=2 Hz,1H,CH); 6.45(d,J=2 Hz,1H,CH); 7.04(d,2H,ArH); 7.29-7.36(m,1H,ArH); 7.61(d,2H,ArH); 7.78(m,1H,ArH); 8.61(m,1H,ArH); 8.71(m,1H,ArH) ppm. NMR (CDCl3): d 44.88; 65.90; 67.70; 90.44; 108.34; 115.29; 123.60; 124.43; 127.13; 131.80; 135.29; 148.99; 149.72; 158.99; 160.39; 163.35; 180.19 ppm.

TLC (silica gel-60, F-254): Rf=0.34, 10% methanol/dichloromethane.

Melting Point: 207.5°-209.5° C.

Infrared (v max, mineral oil): 2925, 1647, 1597, 1561, 1509, 1408, 1254, 1236, 1176, 1014 cm-1.

Ultraviolet (v max, ethanol): 226, 256, 286, 298, 321 nm.

Mass Spectrum: Calculated for C21H20N2O4: 364.1423, Found: 364.1428

Analysis: Calculated for C21H20N2O4: C,69.22; H,5.53; N,7.69, Found: C,68.84; H,5.68; N,7.67.

EXAMPLE 8

2-(4-Morpholinyl)-6-(4-(2-pyridinylmethoxy)phenyl)-4H-pyran-4-one (Compound 6)

2-Morpholinyl-6-(4-hydroxyphenyl)-4-pyrone, as prepared in Example 5, (273 mg, 1.0 mmole) was suspended in 6 ml dimethylformamide in a 25 ml one neck round bottom flask under nitrogen. The suspension was treated with sodium hydride suspension (192 mg, 4.0 mmole) and the reaction mixture was warmed to 55° C. for 40 minutes. The reaction was treated with 2-picolyl chloride hydrochloride (492 mg, 3.0 mmole) and the mixture was stirred 4 hours at 55° C. The reaction was poured into 50 ml 2N sodium hydroxide/ice and the precipitated solid was collected, washed with water and diethyl ether and was dried (188 mg). The crude material was recrystallized from ethyl acetate to give 123 mg (34%) of Compound 6 as an off-white solid.

H-NMR (CDCl3,TMS): d 3.42(m,4H,CH2); 3.84(m,4H,CH2); 5.26(s,2H,ArCH2); 5.42(d,J=2 Hz,1H,CH); 6.45(d,J=2 Hz,1H,CH); 7.06(d,2H,ArH); 7.24-7.28(m,1H,ArH); 7.50(d,1H,ArH); 7.60(d,2H,ArH); 7.74(m,1H,ArH); 8.62(m,1H,ArH) ppm.

C-NMR (CDCl3): d 44.76; 65.78; 70.69; 90.34; 108.16; 115.23; 121.25; 122.78; 124.11; 126.95; 136.81; 149.26; 156.29; 158.95; 160.36; 163.22; 180.09 ppm.

TLC (silica gel-60, F-254): Rf=0.34, 10% methanol/dichloromethane.

Melting Point: 200°-201° C.

Infrared (v max, mineral oil): 2925, 1649, 1598, 1563, 1513, 1407, 1261, 1248, 1222, 1191, 1117 cm-1.

Ultraviolet (v max, ethanol): 226, 256, 280, 286, 298, 321 nm.

Mass Spectrum: Calculated for C21H20N2O4: 364.1423; Found: 364.1429.

EXAMPLE 9

2-(4-Morpholinyl)-6-((4-(2-(1-piperidinyl)ethyl)oxy)-phenyl)-4H-pyran-4-one (Compound 7)

2-Morpholinyl-6-(4-hydroxyphenyl)-4-pyrone, as prepared in Example 5, (273 mg, 1.0 mmole) was suspended in 8 ml acetonitrile in a 25 ml one neck round bottom flask under nitrogen. The suspension was treated successively with potassium carbonate (829 mg, 6.0 mmole) and N-chloroethyl-piperidine (466 ul, 3.0 mmole) and the reaction mixture was warmed at 70° C. for 5 hours. The acetonitrile was removed in vacuo and the residue was washed with 1×25 ml dichloromethane. The insoluble material was removed by filtration and the filtrate was concentrated in vacuo to an amber oil. The oil was crystallized from diethyl ether and was recrystallized twice from ethyl acetate to provide 147 mg (38%) of Compound 7.

H-NMR (CDCl3,TMS): d 1.38-1.67(m,6H,CH2); 2.31-2.58(m,4H,CH2); 2.79(t,J=6 Hz,2H,CH2); 3.42(m,4H,CH2); 3.85(m,4H,CH2); 4.15(t,J=6 Hz,2H,CH2); 5.42(d,J=2 Hz,1H,CH); 6.45(d,J=2 Hz,1H,CH); 6.98(d,2H,ArH); 7.60(d,2H,ArH) ppm.

C-NMR (CDCl3): d 24.01; 25.79; 44.76; 54.97; 57.62; 65.78; 66.14; 90.29; 107.95; 114.92; 123.59; 126.84; 159.13; 160.89; 163.22; 180.15 ppm.

TLC (silica gel-60, F-254): Rf=0.27, 10% methanol/dichloromethane.

Melting Point: 141.5°-142.0° C.

Infrared (v max, mineral oil): 2925, 1654, 1606, 1568, 1511, 1407, 1366, 1253, 1235, 1193, 1121 cm-1.

Ultraviolet (v max, ethanol): 226, 256, 286, 299, 322 nm.

Mass Spectrum: Calculated for C22H28N2O4: 384.2049; Found: 384.2041.

EXAMPLE 10

2-(4-Morpholinyl)-6-(4-(2-quinolinylmethoxy)phenyl)-4H-pyran-4-one (Compound 8)

2-Morpholinyl-6-(4-hydroxyphenyl)-4-pyrone, as prepared in Example 5, (273 mg, 1.0 mmole) was suspended in 8 ml acetonitrile in a 25 ml one neck round bottom flask under nitrogen. The suspension was treated successively with potassium carbonate (829 mg, 6.0 mmole) and 2-chloromethyl-quinoline (533 mg, 3.0 mmole). The reaction mixture was stirred at 70° C. overnight. The acetonitrile was removed in vacuo and the residue was washed with 1×25 ml dichloromethane. The insoluble material was removed by filtration and the filtrate was concentrated in vacuo to a yellow solid. The crude material was washed with diethyl ether and was recrystallized from ethyl acetate to give 377 mg (91%) of Compound 8 as an orange solid.

H-NMR (CDCl3,TMS): d 3.40(m,4H,CH2); 3.82(m,4H,CH2); 5.44(s,2H,ArCH2); 5.45(d,J=2 Hz,1H,CH); 6.45(d,J=2 Hz,1H,CH); 7.09(d,2H,ArH); 7.55-7.66(m,4H,ArH); 7.76(m,1H,ArH); 7.74(d,1H,ArH); 8.10(d,1H,ArH); 8.21(d,1H,ArH) ppm.

C-NMR (CDCl3): d 44.75; 65.77; 71.30; 90.27; 108.02; 115.33; 118.89; 124.11; 126.66; 126.99; 127.50; 127.63; 128.75; 129.89; 137.16; 147.36; 156.87; 158.98; 160.40; 163.20; 179.99 ppm.

TLC (silica gel-60, F-254): Rf=0.47, 10% methanol/dichloromethane.

Melting Point: 222.5°-223.5° C.

Infrared (v max, mineral oil): 2924, 1643, 1602, 1561, 1507, 1454, 1249, 1178, 1118, 831 cm-1.

Ultraviolet (v max, ethanol): 205, 228, 256, 285, 295, 303, 309, 317, 326 nm.

Mass Spectrum: Calculated for C25H22N2O4: 414.1579; Found: 414.1588.

EXAMPLE 11

2-(4-Morpholinyl)-6-(2-(phenylmethoxy)phenyl)-4H-pyran-4-one (Compound 9)

2-Bromophenol (6.7 ml, 57.8 mmole) was dissolved in 200 ml acetonitrile in a 500 ml one neck round bottom flask under nitrogen. The solution was treated successively potassium carbonate (32 g, 231 mmole) and benzyl bromide (6.9 ml, 57.8 mmole). The reaction mixture was stirred for 6 hours at room temperature. The insoluble salts were removed by filtration and the filtrate was concentrated in vacuo to a pale oil. The oil was taken up in 100 ml diethyl ether and the mixture was washed successively with 2×25 ml 1N sodium hydroxide and 1×25 ml saturated sodium chloride. The organics were dried over magnesium sulfate and were concentrated in vacuo to give 14.8 g (97%) of 2-benzyloxy-bromobenzene as a pale oil.

2-Benzyloxy-bromobenzene (5 g, 19 mmole) and trimethylsilyl-acetylene (3.4 ml, 24 mmole) were combined in 50 ml degassed triethylamine in a 100 ml one neck round bottom flask under nitrogen. The solution was treated successively with bis (triphenylphosphine) palladium dichloride (533 mg, 0.76 mmole) and cuprous iodide (72 mg, 0.38 mmole) and the reaction was heated to 80° C. for 3 hours. The mixture was cooled to room temperature and the volatiles were removed in vacuo. The black residue was washed with diethyl ether and the insoluble material was removed by filtration. The filtrate was concentrated in vacuo to a dark brown oil. The oil was dissolved in 30 ml methanol in a 100 ml one neck round bottom flask under nitrogen. The solution was treated with 1×10 ml 2N sodium hydroxide and the reaction mixture was stirred 1 hour at room temperature. The reaction was treated with DARCO and was filtered through celite. The filtrate was concentrated in vacuo to an aqueous residue. The residue was extracted with 3×20 ml diethyl ether and the combined organics were dried over magnesium sulfate. The organics were concentrated in vacuo to provide a crude yellow oil (3.32 g).

The oil was chromatographed over 120 g silica gel (230–400 mesh) eluting with 1% ethyl acetate/hexane and collecting 16 ml fractions. Fractions 80–86 were combined and concentrated to afford 786 mg (20%) of 2-benzyloxyphenyl acetylene as a yellow oil.

2-Benzyloxyphenyl acetylene (760 mg, 3.65 mmole) was dissolved in 12 ml dry tetrahydrofuran in an oven dried 50 ml two neck round bottom flask under nitrogen. The solution was cooled to −78° C. and was treated slowly dropwise with butyllithium (2.3 ml, 3.65 mmole). The reaction mixture was stirred 30 minutes at −78° C., was warmed to 0° C. for 30 minutes, and was recooled to −78° C. The reaction was treated with methyl chloroformate (0.50 ml, 6.47 mmole) and the mixture was warmed to 0° C. for 30 minutes. The reaction was diluted with 50 ml diethyl ether and was quenched with 1×20 ml 1:1 saturated ammonium chloride/saturated sodium chloride. The layers were separated and the aqueous layer was washed with 2×20 ml diethyl ether. The combined organics were dried over magnesium sulfate and were concentrated in vacuo to a crude yellow oil.

The oil was chromatographed over 42 g silica gel (230–400 mesh) eluting with 8% ethyl acetate/hexane and collecting 9 ml fractions. Fractions 30–48 were combined and concentrated to afford 620 mg (62%) of methyl-(2-benzyloxyphenyl)-propioplate as a yellow oil.

Acetyl morpholine (546 ul, 4.72 mmole) was dissolved in 10 ml dry tetrahydrofuran in an oven dried 50 ml two neck round bottom flask under nitrogen. The solution was cooled to 0° C. and was treated slowly dropwise with lithium diisopropylamide (3.2 ml, 4.72 mmole). The mixture was stirred 30 minutes at 0° C. and was treated with methyl-2-benzyloxyphenyl propiolate (600 mg, 2.25 mmole) in 2 ml dry tetrahydrofuran. The reaction mixture was stirred for 1 hour at 0° C. and was diluted with 10 ml water. The volatiles were removed in vacuo and the residue was crystallized from diethyl ether/methanol (20:1). The tan solid was collected, was washed with diethyl ether, and was dried to afford 500 mg (61%) of morpholine-5-(2-Benzyloxyphenyl)-3-oxopent-4-ynamide as a tan solid. Melting Point: 224°–227° C.

Acetylenic ketoamide, just prepared above, (480 mg, 1.32 mmole) was dissolved in 5 ml trifluoroacetic acid in a 25 ml one neck round bottom flask under nitrogen. The reaction mixture was stirred 2 hours at room temperature and was poured into 50 ml 2N sodium hydroxide. The mixture was extracted with 4×25 ml dichloromethane and the combined organics were dried over magnesium sulfate. The organics were concentrated in vacuo to a dark yellow oil.

The oil was chromatographed over 18 g silica gel (230–400 mesh) eluting with 3% methanol/dichloromethane and collecting 4 ml fractions. Fractions 21–32 were combined and concentrated to afford 227 mg (47%) of Compound 9 as a yellow solid.

H-NMR (CDCl3,TMS): d 3.30(m,4H,CH2); 3.69(m,4H,CH2); 5.17(s,2H,ArCH2); 5.55(d,J=2 Hz,1H,CH); 6.71(d,J=2 Hz,1H,CH); 7.06(m,2H,ArH); 7.30–7.44(m,6H,ArH); 7.53(m,1H,ArH) ppm. C-NMR (CDCl3): d 44.64; 65.72; 70.51; 90.04; 113.20; 113.53; 120.97; 127.08; 128.14; 128.62; 129.06; 131.87; 135.99; 156.39; 157.79; 163.46; 180.01 ppm.

TLC (silica gel-60, F-254): Rf=0.47, 10% methanol/dichloromethane.

Melting Point: 112.5°–113° C.

Infrared (v max, mineral oil): 2923, 1643, 1600, 1561, 1454, 1411, 1244, 1119 cm-1.

Ultraviolet (v max, ethanol): 210, 245, 270, 281, 309 nm.

Mass Spectrum: Calculated for C22H21NO4: 363.1470; Found: 363.1466

Analysis: Calculated for C22H21NO4: C,72.71; H,5.82; N,3.85; Found: C,72.78; H,6.01; N,4.08.

Following the general procedure for Example 11, but starting with the appropriate bromobenzene, there are prepared the following products:

2-(4-(hydroxymethyl)phenyl)-6-(4-morpholinyl)-4H-pyran-4-one (Compound 17), mp 258°–259.5° C.;

2-(4-morpholinyl)-6-(4-(1-piperidinylmethyl)phenyl)-4H-pyran-4-one (Compound 18), mp 194°–195.5° C.;

2-(4-morpholinyl)-6-(4-(1-pyrrolidinylmethyl)phenyl)-4H-pyran-4-one(Compound 19), mp 168°–169.5° C.;

2-(4-((4-methyl-1-piperazinyl)methyl)phenyl)-6-(4-morpholinyl)-4H-pyran-4-one(Compound 20), mp 161.5°–163° C.;

2-(4-((2-(hydroxymethyl)-1-piperidinyl)methyl)phenyl-6-(4-morpholinyl)-4H-pyran-4-one (Compound 21), mp 160.5°–161.5° C.

EXAMPLE 12

2-(2-Hydroxyphenyl)-6-(4-morpholinyl)-4H-pyran-4-one (Compound 10)

6-((2-Benzyloxy)-phenyl)-2-morpholinyl-4-pyrone (100 mg, 0.275 mmole) was dissolved in 5 ml methanol in a 10 ml one neck round bottom flask under nitrogen. The solution was treated with 10% palladium on carbon (100 mg) and cyclohexene (1 ml, 15 mmole) and the reaction mixture was heated to reflux for 30 minutes. The reaction was filtered hot through celite and the filter cake was washed well with fresh hot methanol. The filtrate was concentrated in vacuo to a yellowish crude solid. The solid was recrystallized from methanol to afford 34 mg (45%) of Compound 10 as a white crystalline solid.

H-NMR (d6DMSO): d 3.36(m,4H,CH2); 3.68(m,4H,CH2); 5.36(d,J=2Hz,1H,CH); 6.66(d,J=2Hz,1H,CH); 6.88–6.98(m,2H,ArH); 7.26–7.31(t,1H,ArH); 7.60(d,1H,ArH); 10.5(bs,1H,OH) ppm.

C-NMR (d6DMSO): d 46.11; 67.03; 90.91; 114.47; 118.56; 119.33; 121.09; 129.55; 133.32; 157.59; 157.78; 164.74; 180.32 ppm.

TLC (silica gel-60, F-254): Rf=0.33, 10% methanol/dichloromethane.

Melting Point:>250° C.

Infrared (v max, mineral oil): 2925, 2855, 1638, 1567, 1544, 1445, 1400, 1234, 1126, 763 cm−1.

Mass Spectrum: Calculated for C15H15NO4: 273.1001; Found: 273.0999

Analysis: Calculated for C15H15NO4: C,65.92; H,5.53; N,5.12; Found: C,65.93; H,5.60; N,5.39.

EXAMPLE 13

2-(4-Morpholinyl)-6-(4-((1-phenylpentyl)oxy)phenyl)-4H-pyran-4-one (Compound 11)

Dibromo-olefin from Example 4 (20 g, 54 mmole) was dissolved in 250 ml dry tetrahydrofuran in an oven dried 500 ml three neck round bottom flask under nitrogen. The solution was cooled −78° C. and was treated dropwise with butyllithium (80 ml, 128 mmole). The reaction was stirred 40 minutes at −78° C. and was warmed to 0° C. for 1 hour. The reaction was recooled to −78° C. and was treated with methyl chloroformate (4.95 ml, 64 mmole). The reaction mixture was stirred overnight as the cooling bath expired. The mixture was quenched with 1×50 ml 1:1 saturated ammonium chloride/saturated sodium bicarbonate. The terahydrofuran/hexane was removed in vacuo and the residue was extracted with 4×50 ml ethyl acetate. The combine organics were dried over magnesium sulfate and were concentrated in vacuo to a reddish oil.

The oil was chromatographed over 600 g silica gel (230–400 mesh) eluting with 10% ethyl acetate/hexane and after a 2000 ml forerun collecting 75 ml fractions. Fractions 1–12 were combined and concentrated to afford 6.4 g (37%) of butylated benzyloxyphenyl propiolate methyl(4-αbutylbenzyloxy)-phenylpropiolate as a white solid. Fractions 15–38 were combined and concentrated to provide 4.5 g (35%) of 4-benzyloxyphenyl propiolate as a white solid. Melting Point: 45°–47.5° C.

Acetyl morpholine (2.43 ml, 21 mmole) was dissolved in 30 ml dry tetrahydrofuran in an oven dried 100 ml two neck round bottom flask under nitrogen. The solution was cooled to 0° C. and was treated slowly dropwise with lithium diisopropylamide (14 ml, 21 mmole). The reaction was stirred 30 min at 0 C. and was treated with phenyl propiolate, prepared above, (3.22 g, 10 mmole) in one lot. The reaction mixture was stirred 1 hour at 0° C. The mixture was diluted with 50 ml water and the organic volatiles were removed in vacuo, The precipitated solid was collected and was washed successively with water and diethyl ether. The solid was dried in vacuo overnight at 40° C. to provide 3.3 g (79%) of morpholine-5-((4-α-Butylbenzyloxy)-phenyl)-3-oxo-pent-4-ynamide as a yellow solid. Melting Point: 271°–273° C.

The acetylenic ketoamide, prepared above, (1.23 g, 3.0 mmole) was dissolved in 18 ml 15% trifluoroacetic acid/dichloromethane in a 50 ml one neck round bottom flask under nitrogen. The solution was stirred 15 minutes at room temperature and the reaction mixture was poured into saturated sodium bicarbonate. The mixture was extracted with 3×25 ml dichloromethane. The combined organics were dried over magnesium sulfate and were concentrated in vacuo to a yellow paste. The aqueous layer was filtered to collect the precipitated product which was washed with water and diethyl ether and was recrystallized from methanol to afford 451 mg (55%) of the phenol.

The yellow paste was chromatographed over 18 g silica gel (230–400 mesh) eluting with 4% methanol/dichloromethane and collecting 5 ml fractions. Fractions 21–26 were combined and concentrated to provide 41 mg (3%) of Compound 11 as a yellow solid.

H-NMR (CDCl3,TMS): d0.90(t,3H,CH3); 1.29–1.57(m,4H,CH2); 1.79–1.89(m,1H,CH); 1.97–2.09(m,1H,CH); 3.46(m,4H,CH2); 3.82(m,4H,CH2); 5.13(dd,1H,ArCH); 5.74(bs,1H, CH); 6.53(d,1H,CH); 6.92(d,2H,ArH); 7.24–7.39(m,5H,ArH); 7.50(d,2H,ArH) ppm.

C-NMR (CDCl3): d 13.98; 22.49; 27.83; 38.35; 45.04; 65.80; 80.77; 89.05; 105.03; 116.50; 122.34; 125.86; 127.28; 127.78; 128.72; 141.28; 160.72; 161.30; 163.42; 178.47 ppm.

TLC (silica gel-60, F-254): Rf=0.39, 10% methanol/dichloromethane.

Melting Point: 185°–186° C.

Infrared (v max, mineral oil): 2925, 1646, 1605, 1563, 1507, 1452, 1417, 1254, 1178, 1118, 830 cm−1.

Ultraviolet (v max, ethanol): 228, 257, 288, 300, 322 nm.

Mass Spectrum: Calculated for C26H29NO4: 419.2096; Found: 419.2103.

Analysis: Calculated for C26H29NO4: C,74.44; H,6.97; N,3.34; Found: C,74.56; H,7.22; N,3.70.

EXAMPLE 14

2-(4-hydroxyphenyl)-6-(4-morpholinylmethyl)-4H-pyran-4-one (Compound 14)

Phenylacetylmethyl sulfoxide (5.65 g, 31 mmol) was dissolved in 60 ml THF in a flame dried 3-neck flask under nitrogen. The solution was cooled to −78° C. and treated dropwise with lithium diisopropylamide (41 ml, 62 mmol, 1.5M in THF/heptane). The mixture was stirred 20 minutes at −78° C., followed by 30 minutes at 0° C. and recooled to −78° C. Methyl 4-benzyloxyphenyl propiolate (3.5 g, 15.5 mmol) was added and the reaction was stirred at −78° C. for 30 minutes and then at 0° C. for 30 minutes. The mixture was quenched with 50 ml water and the THF was removed in vacuo. The orange precipitate was collected and washed with water and ether. The solid was dried overnight in vacuo to give 4.77 g (74%) of the diketone, mp.>300° C.

The diketone (4.77 g, 11.45 mmol) was dissolved in 230 ml of methanol and stirred at room temperature for 28 hours. The methanol was removed in vacuo and the solid residue was dissolved in methylene chloride and filtered through a plug of celite. The filtrate was concentrated in vacuo to a tan solid. The solid was chromatographed over 200 g of silica gel, eluting with 4% methanol/methylene chloride and collecting 60 ml fractions. Fractions 14–25 were combined and concentrated to afford 2.99 g (63%) of the pyrone sulfoxide as a tan solid, mp. 155°–156° C.

The pyrone sulfoxide (840 mg, 2 mmol) was suspended in 6 ml of acetic anhydride under nitrogen. The mixture was heated to 105° C. for 4 hours, poured into 10 ml water and shaken vigorously. The mixture was diluted with 10 ml of saturated NaCl and extracted 4×20 ml methylene chloride. The combined organics were dried over magnesium sulfate and concentrated to a dark oil. The oil was chromatographed over 32 g of silica gel eluting with 55% ethyl acetate/hexane to afford 769 mg of a dark oil. Crystallization from ether afforded 679 mg (74%) of the acetoxysulfide pyrone as a tan solid, mp. 117°–119° C.

The acetoxysulfide pyrone (1.12 g, 2.44 mmol) was suspended in 20 ml methanol under nitrogen. The mixture was cooled to 0° C., treated with 450 mg of sodium borohydride, and warmed to room temperature. The addition of sodium borohydride was repeated three times and the mixture was concentrated to dryness. The residue was diluted with 50 ml of 10% HCl and the insoluble material was collected, washed with water and ether and dried in vacuo at 40° C. to provide 688 mg (91%) of the pyrone alcohol, mp. 166°–167° C.

The pyrone alcohol (173 mg (0.56 mmol) was suspended in 5 ml of chloroform under nitrogen. The mixture was cooled to 0° C. and treated with triethylamine (0.117 ml, 0.84 mmol), tosyl chloride (160 mg, 0.84 mmol) and dimethylaminopyridine 7 mg, 0.06 mmol). The reaction was warmed to room temperature and stirred 2 h. The mixture was diluted with 20 ml of methylene chloride and washed with 10 ml saturated sodium bicarbonate, 10 ml 5% HCl, and 10 ml of saturated NaCl. The organics were dried over magnesium sulfate and concentrated to a green oil. The oil was crystallized from 1:1 ether/hexane to provide 188 mg of a mixture of the pyrone tosylate and pyrone chloride as a green solid.

The mixture of the pyrone tosylate and pyrone chloride (188 mg) was dissolved in 2 ml morpholine under nitrogen. The mixture was stirred 1 hour at room temperature and the morpholine was removed in vacuo at 40° C. The residue was washed with 10 ml 1N NaOH and the insoluble material was collected. The solid was washed with water and ether to give 150 mg. The crude material was recrystallized from ethylacetate to give 145 mg (71%) Compound 14 as amber flakes, mp. 162.5°–163.5° C.

Following the general procedure for example 15, there are prepared the following products:
2-(4-morpholinyl)-6-(3-(phenylmethoxy)phenyl)-4H-pyran-4-one(Compound 15, mp 170.5°–171.5° C.;
2-(3-hydroxyphenyl)-6-(4-morpholinyl)-4H-pyran-4-one(Compound 16), mp 255.5°–256° C.

EXAMPLE 15

2-(4-Fluorophenyl)-6-(4-morpholinyl)-4H-pyran-4-one (Compound 22)

Compound 22 was prepared according to Scheme 2 where the phenylmethoxy group was substituted with a fluoride. Melting Point 214°–215° C.

EXAMPLE 16

2-(4-Morpholinyl)-6-4-(1-pyrrolidinyl)phenyl-4H-pyran-4-one (Compound 23)

Compound 23 was prepared as in Example 15 where the fluorine was then replaced with a pyrrolidine by direct substitution. Melting Point 279° C.

EXAMPLE 17

2-(4-Morpholinyl)-6-4-(1-piperidinyl)phenyl-4H-pyran-4-one (Compound 24)

Compound 24 was prepared as in Example 15 with the fluorine being replaced with a piperidine by direct substitution. Melting Point 260°–262° C.

EXAMPLE 18

2-(4-Aminophenyl)-6-(4-morpholinyl)-4H-pyran-4-one (Compound 25)

The subject compound was prepared following Scheme IV as follows. A solution of acetylacetylmorpholine (3.42 g, 20 mmol) in 20 ml of tetrahydrofuran was treated with sodium hydride (0.8 g, 20 mmol, 60% in oil) and stirred at room temperature for 30 minutes. The mixture was cooled to 0° C., treated with n-butyl lithium in hexane (12.9 ml, 20 mmol, 1.6M) and stirred for 30 minutes. The mixture was treated with 1.51 g (10 mmol) of methyl 4-aminobenzoate, stirred 1 hours at 0° C. and 1 hour at room temperature. The mixture was quenched with 3.1 ml of trifluoroacetic acid and the volatiles were removed in vacuo. The residue was chromatographed over 150 g of silica gel, eluting with 4% methanol/methylene chloride to afford 0.80 g (28%) of the intermediate tricarbonyl compound, mp=167°–168° C. The tricarbonyl compound (0.94 g, 3.26 mmol) was dissolved in 6.5 ml of concentrated sulfuric acid and heated at 70° C. for 40 min. The mixture was allowed to cool, added slowly to excess sodium bicarbonate in water. The insoluble material was collected, washed with water and dried. The solid was recrystallized from ethyl acetate/methanol to afford 0.64 g (72%) of the title compound, Melting Point: 257.5°–259.5° C.

Synthesis of 2-Amino-6-Phenyl-4H-Pyran-4-ones
Schemes

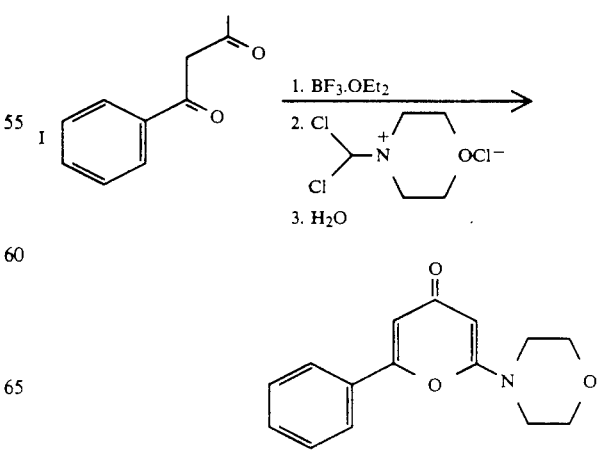

-continued
Synthesis of 2-Amino-6-Phenyl-4H-Pyran-4-ones Schemes

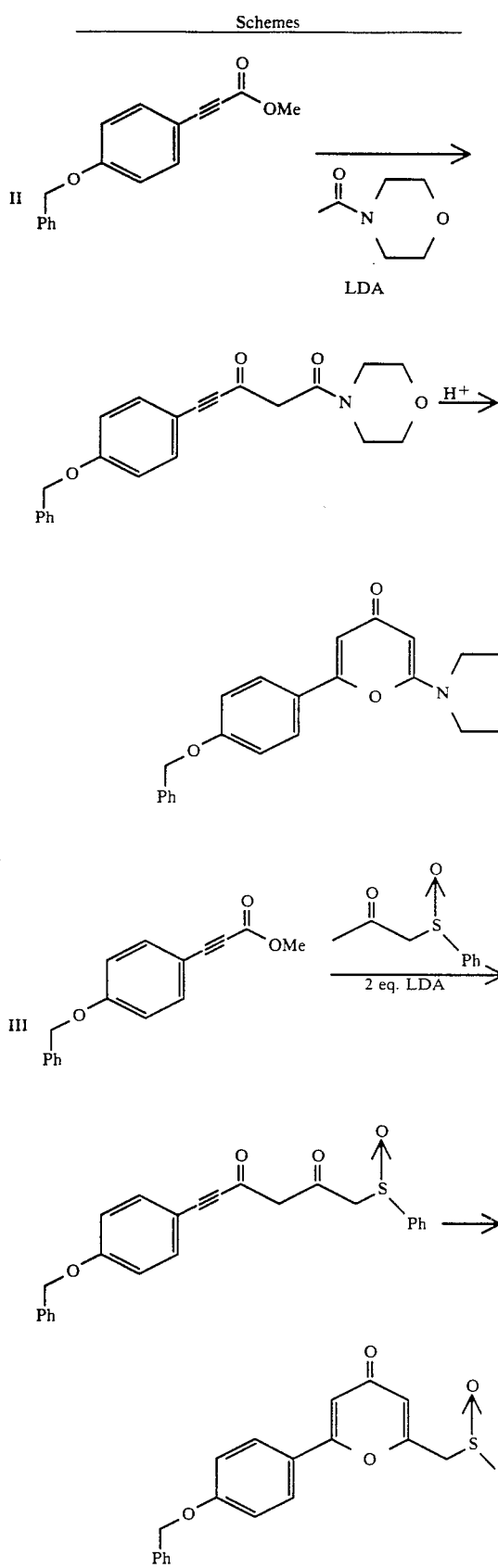

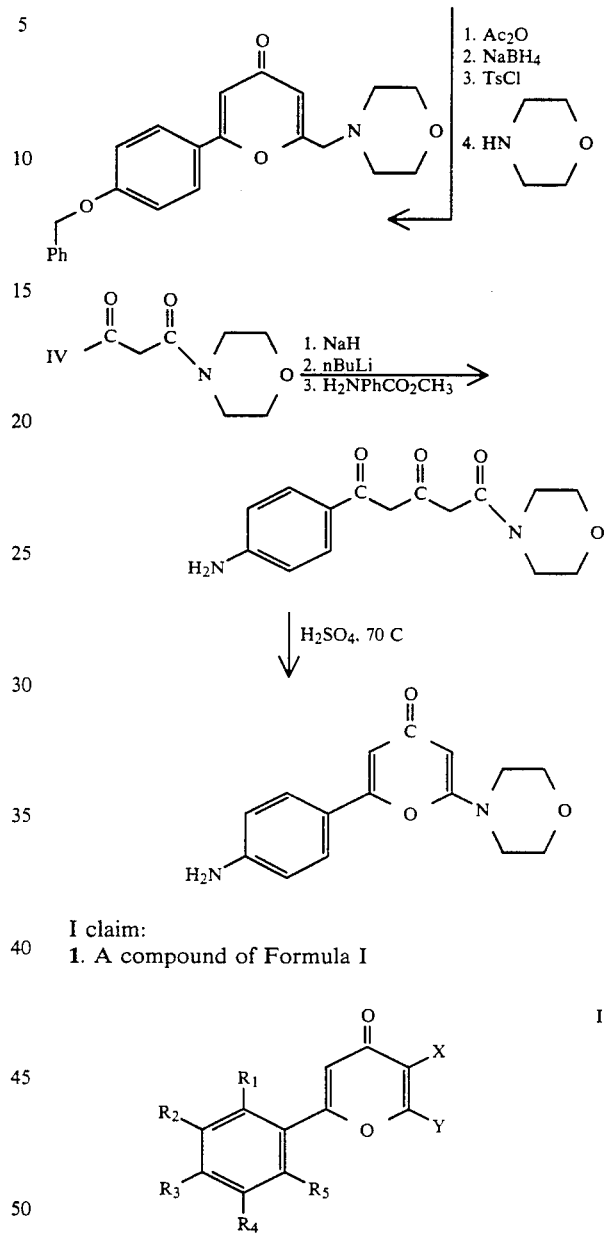

I claim:
1. A compound of Formula I or pharmaceutically acceptable salt thereof,
wherein:
X is hydrogen, $C_1$–$C_5$ alkyl, or a halogen atom;
Y is selected from the group consisting of
—$(CH_2)_n NR_9 R_{10}$ wherein $R_9$ and $R_{10}$, are independently selected from the group consisting of
  (a) hydrogen;
  (b) $C_1$–$C_{12}$ alkyl;
  (c) phenyl optionally substituted with one, 2 or 3 $C_1$–$C_4$ alkyl, $C_1$–$C_4$ alkoxy, halo, OH, trifluoromethyl or —$CO_2(C_1$–$C_4$ alkyl);
  (d) —$(CH_2)_q$phenyl wherein phenyl is optionally substituted with one, 2 or 3 $C_1$–$C_4$ alkyl, $C_1$–$C_4$ alkoxy, halo, OH, trifluoromethyl or —$CO_2(-C_1$–$C_4$alkyl);
  (e) —$(CH_2)_n$pyridinyl; or (f) wherein $R_9$ and $R_{10}$, taken together with N, form a saturated or unsaturated heterocyclic amine ring selected from the group consisting of (aa) 4-morpholine optionally substituted with one or two members selected from the group consisting of $C_1$-$C_4$ alkyl, $C_1$-$C_4$ alkoxy, halo or trifluoromethyl, (bb) 4-thiomorpholine optionally substituted with one or two members selected from the group consisting of $C_1$-$C_4$ alkyl, $C_1$-$C_4$ alkoxy, halo or trifluoromethyl, (cc) 3-amino-1-pyrrolidine, (dd) 1-pyrrolidine optionally substituted with one or two members selected from the group consisting of $C_1$-$C_4$ alkyl, $C_1$-$C_4$ alkyl, halo, OH, —$CH_2OH$, or trifluoromethyl, (ee) 1-piperidine optionally substituted with one or two members selected from the group consisting of $C_1$-$C_4$ alkyl, $C_1$-$C_4$ alkoxy, halo, trifluoromethyl, —$(CH_2)_qOH$, —$CO_2H$, —$CO_2CH_3$, —$CO_2CH_2CH_3$ or phenyl (wherein phenyl is optionally substituted with one, 2 or 3 $C_1$-$C_4$ alkyl, $C_1$-$C_4$ alkoxy, halo or trifluoromethyl), (ff) 1-piperazine, 4-methyl-1-piperazine, 4-(cycloC$_3$-C$_6$alkyl)-1-piperazine, 4-phenyl-1-piperazine (wherein phenyl is optionally substituted with one, 2 or 3 $C_1$-$C_4$ alkyl, $C_1$-$C_4$ alkoxy, halo or trifluoromethyl) or 4-pyridinyl-1-piperazine optionally substituted with one or two members selected from the group consisting of $C_1$-$C_4$ alkyl, $C_1$-$C_4$ alkoxy, halo, OH, trifluoromethyl, —$CH_2OH$, —$CO_2H$, —$CO_2CH_3$ or —$CO_2CH_2CH_3$, and (gg) thiazolidine, thiazolidine-4-carboxylic acid, pipecolinic acid, p-piperazinacetophenone, 1-piperazine, 1-methylpiperazine, 4-phenyl-1,2,-3,6-tetrahydropyridine, proline, tetrahydrofurylamine, 1-(3-hydroxy)pyrrolidine, nipecotamide, 1,2,3,4-tetrahydroisoquinoline or imidazole;

$R_1$, $R_2$, $R_3$, $R_4$ and $R_5$ are independently selected from the group consisting of: hydrogen, $C_1$-$C_8$ alkyl, —$(CH_2)_n$phenyl (wherein phenyl is optionally substituted with one, 2 or 3 $C_1$-$C_4$ alkyl, $C_1$-$C_4$ alkoxy, halo, OH, trifluoromethyl or —$CO_2$($C_1$-$C_4$alkyl)), —$(CH_2)_n$naphthyl, —$(CH_2)_n$pyridinyl, —$(CH_2)_qNR_9R_{10}$, —CH=CH-phenyl (wherein phenyl is optionally substituted with one, 2 or 3 $C_1$-$C_4$ alkyl, $C_1$-$C_4$ alkoxy, halo, OH, trifluoromethyl or —$CO_2$($C_1$-$C_4$alkyl)),

—$CH_2$—CH=$CH_2$,

—CH=CH—$CH_3$,

—O—$CH_2$—CH=$CH_2$,

—C≡C-phenyl (wherein phenyl is optionally substituted with one, 2 or 3 $C_1$-$C_4$ alkyl, $C_1$-$C_4$ alkoxy, halo, OH, trifluoromethyl or —$CO_2$($C_1$-$C_4$alkyl)), —O(CH$_2$)p(N-methylpiperdin-3-yl), —O—(CH$_2$)pNR$_9$R$_{10}$,

—O—CH$_2$CH(OCH$_3$)$_2$,

—O—(CH$_2$)pOR$_{15}$ (wherein $R_{15}$ is selected from $C_1$-$C_5$ alkyl, —$(CH_2)_n$phenyl (phenyl optionally substituted with one, 2 or 3 $C_1$-$C_4$ alkyl, $C_1$-$C_4$ alkoxy, halo, OH, trifluoromethyl or —$CO_2$($C_1$-$C_4$alkyl)), —$(CH_2)_n$pyridin-yl or —$(CH_2)_p$piperidin-1-yl, —$(CH_2)_nC(O)$—$(CH_2)_nR_9$, —$(CH_2)_nC(O)O$—$(CH_2)_nR_9$, —$(CH)_nC(O)O$—$(CH_2)_pNR_9R_{10}$, —$(CH_2)_nC(O)(CH_2)_nNR_9R_{10}$, $NO_2$, —O—$(CH_2)_nC(O)$—$(CH_2)_nR_9$, —O—$(CH_2)_nC(O)O$—$(CH_2)_nR_9$, —O—$(CH_2)_nC(O)$—$(CH_2)_nNR_9R_{10}$,

—$NR_9R_{10}$,

—$N(R_9)(CH_2)_nC(O)$—$(CH_2)_nR_{10}$,

—$N(R_9)$—$(CH_2)_nC(O)O$—$(CH_2)_nR_{10}$, $N(R_9)(CH_2)_nC(O)$—$(CH_2)_nNR_9R_{10}$,

—$OCH(C_4H_9)$phenyl,

—O—$(CH_2)_n$phenyl (wherein phenyl is optionally substituted with one, 2 or 3 $C_1$-$C_4$ alkyl, $C_1$-$C_4$ alkoxy, halo, OH, trifluoromethyl or —$CO_2$($C_1$-$C_4$alkyl)), —O—$(CH_2)_n$pyridine, —$O(CH_2)_nC(O)$—$(CH_2)_n$pyridine, —O—$(CH_2)_nC(O)O$—$(CH_2)_n$pyridine, —$O(CH_2)_nC(O)$—$N(R_9)(CH_2)_n$pyridine, —O—$(CH_2)_n$quinoxalinyl, —O—$(CH_2)_n$quinolinyl, —O—$(CH_2)_n$pyrazinyl, —O—$(CH_2)_n$naphthyl, —O—$(CH_2)_nC(O)$—$(CH_2)_n$naphthyl, —O—$(CH_2)_nC(O)O$—$(CH_2)_n$naphthyl, —O—$(CH_2)_nC(O)NR_9$—$(CH_2)_n$naphthyl, halo,

OH,

—$(CH_2)_q$—OH, $(CH_2)_qOC(O)R_9$,

—$(CH_2)_qOC(O)$—$NR_9R_{10}$,

-(1-cyclohexyl-1H-tetrazol-5-yl)$C_1$-$C_4$ alkoxy,

-(1-($C_1$-$C_5$alkyl)-1H-tetrazol-5-yl)$C_1$-$C_4$ alkoxy,

-(1-(phenyl)-1H-tetrazol-5-yl) $C_1$-$C_4$ alkoxy (wherein phenyl is optionally substituted with one, 2 or 3 $C_1$-$C_4$ alkyl, $C_1$-$C_4$ alkoxy, halo, OH, trifluoromethyl or —$CO_2(C_1$-$C_4$alkyl)), -(1-(pyridinyl)-1H-tetrazol-5-yl)$C_1$-$C_4$ alkoxy, -(1-(1-phenylethyl)-1H-tetrazol-5-yl)$C_1$-$C_4$ alkoxy, -$C_1$-$C_4$ alkoxyl;

n is 0-5;

p is 2-5; and q is 1-5.

2. The compound of claim 1 wherein X is hydrogen.

3. The compound of claim 1 wherein Y is $(CH_2)_n$-4-morpholine where n is 0 or 1.

4. The compound of claim 3 wherein $R_1$, $R_2$, $R_4$ and $R_5$ are hydrogen.

5. The compound of claim 4 which is a) 2-(4-hydroxyphenyl)-6-(4-morpholinyl)-4H-pyran-4-one;

b) 2-(4-morpholinyl)-6-(4-(phenylmethoxy)phenyl)-4H-pyran-4-one;

c) 2-(4-morpholinyl)-6-phenyl-4H-pyran-4-one;

d) 2-(4-(3,3-dimethyl-2-oxobutoxy)phenyl)-6-(4-morpholinyl)-4H-pyran-4-one;

e) 2-(4-morpholinyl)-6-(4-(3-pyridinylmethoxy)-phenyl)-4H-pyran-4-one;

f) 2-(4-Morpholinyl)-6-(4-(2-pyridinylmethoxy)-phenyl)-4H-pyran-4-one;

g) 2-(4-Morpholinyl)-6-((4-(2-(1-piperidinyl)ethyl)oxy)phenyl)-4H-pyran-4-one;

h) 2-(4-Morpholinyl)-6-(4-(2-quinolinylmethoxy)-phenyl)-4H-pyran-4-one;
i) 2-(4-Morpholinyl)-6-(2-(phenylmethoxy)phenyl)-4H-pyran-4-one;
j) 2-(2-Hydroxyphenyl)-6-(4-morpholinyl)-4H-pyran-4-one;
k) 2-(4-Morpholinyl)-6-(4-((1-phenylpentyl)oxy)-phenyl)-4H-pyran-4-one;
l) 2-(4-morpholinylmethyl)-6-(4-(phenylmethoxy)-phenyl)-4H-pyran-4-one;
m) 2-(4-(phenylmethoxy)phenyl)-6-(1-piperidinylmethyl)-4H-pyran-4-one;
n) 2-(4-hydroxyphenyl)-6-(4-morpholinylmethyl)-4H-pyran-4-one;
o) 2-(4-morpholinyl)-6-(3-(phenylmethoxy)phenyl)-4H-pyran-4-one;
p) 2-(3-hydroxyphenyl)-6-(4-morpholinyl)-4H-pyran-4-one;
q) 2-(4-(hydroxymethyl)phenyl)-6-(4-morpholinyl)-4H-pyran-4-one;
r) 2-(4-morpholinyl)-6-(4-(1-piperidinylmethyl)-phenyl)-4H-pyran-4-one;
s) 2-(4-morpholinyl)-6-(4-(1-pyrrolidinylmethyl)-phenyl)-4H-pyran-4-one;
t) 2-(4-((4-methyl-1-piperazinyl)methyl)phenyl)-6-(4-morpholinyl)-4H-pyran-4-one;
u) 2-(4-((2-(hydroxymethyl)-1-piperidinyl)methyl)-phenyl)-6-(4-morpholinyl)-4H-pyran-4-one;
v) 2-(4-fluorophenyl)-6-(4-morpholinyl)-4H-pyran-4-one;
w) 2-(4-Morpholinyl)-6-4-(1-pyrrolidinyl)phenyl-4H-pyran-4-one;
x) 2-(4-Morpholinyl)-6-4-(1-piperidinyl)phenyl-4H-pyran-4-one; or
y) 2-(4-Aminophenyl)-6-(4-morpholinyl)-4H-pyran-4-one.

6. A compound of Formula II

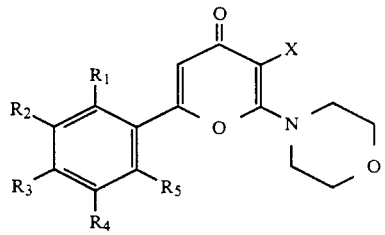

or pharmaceutically acceptable salt thereof, wherein:
X is hydrogen, $C_1$-$C_5$ alkyl, or a halogen atom;
$R_1$, $R_2$, $R_3$, $R_4$ and $R_5$ are independently selected from the group consisting of:
hydrogen,
$C_1$-$C_8$ alkyl,
—$(CH_2)_n$phenyl (wherein phenyl is optionally substituted with one, 2 or 3 $C_1$-$C_4$ alkyl, $C_1$-$C_4$ alkoxy, halo, OH, trifluoromethyl or —$CO_2$(-$C_1$-$C_4$alkyl)),
—$(CH_2)_n$naphthyl,
—$(CH_2)_n$pyridinyl,
—$(CH_2)_q NR_9 R_{10}$,
—CH=CH-phenyl (wherein phenyl is optionally substituted with one, 2 or 3 $C_1$-$C_4$ alkyl, $C_1$-$C_4$ alkoxy, halo, OH, trifluoromethyl or —$CO_2$(-$C_1$-$C_4$alkyl)),
—$CH_2$—CH=$CH_2$,
—CH=CH—$CH_3$,
—O—$CH_2$—CH=$CH_2$,
—C≡C-phenyl (wherein phenyl is optionally substituted with one, 2 or 3 $C_1$-$C_4$ alkyl, $C_1$-$C_4$ alkoxy, halo, OH, trifluoromethyl or —$CO_2$(-$C_1$-$C_4$alkyl)),
—O($CH_2$)p(N-methylpiperdin-3-yl),
—O—$(CH_2)_p NR_9 R_{10}$,
—O—$CH_2 CH(OCH_3)_2$,
—O—$(CH_2)_p OR_{15}$ (wherein $R_{15}$ is selected from $C_1$-$C_5$ alkyl, —$(CH_2)_n$phenyl (phenyl optionally substituted with one, 2 or 3 $C_1$-$C_4$ alkyl, $C_1$-$C_4$ alkoxy, halo, OH, trifluoromethyl or —$CO_2$(-$C_1$-$C_4$alkyl)),
—$(CH_2)_n$pyridin-yl or —$(CH_2)_p$piperidin-1-yl),
—$(CH_2)_n C(O)$—$(CH_2)_n R_9$,
—$(CH_2)_n C(O)O$—$(CH_2)_n R_9$,
—$(CH)_n C(O)O$—$(CH_2)_p NR_9 R_{10}$,
—$(CH_2)_n C(O)(CH_2)_n NR_9 R_{10}$,
$NO_2$,
—O—$(CH_2)_n C(O)$—$(CH_2)_n R_9$,
—O—$(CH_2)_n C(O)O$—$(CH_2)_n R_9$,
—O—$(CH_2)_n C(O)$—$(CH_2)_n NR_9 R_{10}$,
—$NR_9 R_{10}$,
—$N(R_9)(CH_2)_n C(O)$—$(CH_2)_n R_{10}$,
—$N(R_9)$—$(CH_2)_n C(O)O$—$(CH_2)_n R_{10}$,
$N(R_9)(CH_2)_n C(O)$—$(CH_2)_n NR_9 R_{10}$,
—$OCH(C_4 H_9)$phenyl,
—O—$(CH_2)_n$phenyl (wherein phenyl is optionally substituted with one, 2 or 3 $C_1$-$C_4$ alkyl, $C_1$-$C_4$ alkoxy, halo, OH, trifluoromethyl or —$CO_2$(-$C_1$-$C_4$alkyl)),
—O—$(CH_2)_n$pyridine,
—O$(CH_2)_n C(O)$—$(CH_2)_n$pyridine,
—O—$(CH_2)_n C(O)O$—$(CH_2)_n$pyridine,
—O$(CH_2)_n C(O)$—$N(R_9)(CH_2)_n$pyridine,
—O—$(CH_2)_n$quinoxalinyl,
—O—$(CH_2)_n$quinolinyl,
—O—$(CH_2)_n$pyrazinyl,
—O—$(CH_2)_n$naphthyl,
—O—$(CH_2)_n C(O)$—$(CH_2)_n$naphthyl,
—O—$(CH_2)_n C(O)O$—$(CH_2)_n$naphthyl,
—O—$(CH_2)_n C(O)NR_9$—$(CH_2)_n$naphthyl,
halo,
—OH,
—$(CH_2)_q$—OH,
$(CH_2)_q OC(O)R_9$,
—$(CH_2)_q OC(O)$—$NR_9 R_{10}$,
-(1-cyclohexyl-1H-tetrazol-5-yl)$C_1$-$C_4$ alkoxy,
-(1-($C_1$-$C_5$alkyl)-1H-tetrazol-5-yl)$C_1$-$C_4$ alkoxy,
-(1-(phenyl)-1H-tetrazol-5-yl) $C_1$-$C_4$ alkoxy (wherein phenyl is optionally substituted with one, 2 or 3 $C_1$-$C_4$ alkyl, $C_1$-$C_4$ alkoxy, halo, OH, trifluoromethyl or —$CO_2(C_1$-$C_4$alkyl)),
-(1-(pyridinyl)-1H-tetrazol-5-yl)$C_1$-$C_4$ alkoxy,
-(1-(1-phenylethyl)-1H-tetrazol-5-yl)$C_1$-$C_4$ alkoxy,
—$C_1$-$C_4$ alkoxyl;

n is 0-5;
p is 2-5; and
q is 1-5.

7. The compound of claim 6 wherein X is hydrogen.

* * * * *